US012629438B2

(12) United States Patent
Butler et al.

(10) Patent No.: US 12,629,438 B2
(45) Date of Patent: May 19, 2026

(54) SYSTEMS AND METHODS FOR ULTRAVIOLET INTRA-BORE TREATMENT OF MEDICAL IMAGING SYSTEMS

(71) Applicant: THE TRUSTEES OF THE UNIVERSITY OF PENNSYLVANIA, Philadelphia, PA (US)

(72) Inventors: Norman S. Butler, Springfield, PA (US); James J. Pilla, Kennett Square, PA (US); Gabor Mizsei, Swarthmore, PA (US); Terence Peter Gade, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 641 days.

(21) Appl. No.: 18/008,328

(22) PCT Filed: Jun. 4, 2021

(86) PCT No.: PCT/US2021/035935
§ 371 (c)(1),
(2) Date: Dec. 5, 2022

(87) PCT Pub. No.: WO2021/248021
PCT Pub. Date: Dec. 9, 2021

(65) Prior Publication Data
US 2023/0285610 A1      Sep. 14, 2023

Related U.S. Application Data

(60) Provisional application No. 63/035,202, filed on Jun. 5, 2020.

(51) Int. Cl.
*A61L 2/00*         (2006.01)
*A61L 2/10*         (2006.01)
(Continued)

(52) U.S. Cl.
CPC .................. *A61L 2/10* (2013.01); *A61L 2/24* (2013.01); *B08B 1/143* (2024.01); *B08B 7/0057* (2013.01);
(Continued)

(58) Field of Classification Search
CPC .......... A61L 2/10; A61L 2/24; A61L 2202/24; A61L 2202/16; A61L 2202/11; A61B 6/4423
(Continued)

(56) References Cited

U.S. PATENT DOCUMENTS 5,918,342 A *   7/1999   Smith ................... G01R 33/28
                                                    15/228
2015/0158741 A1   6/2015   Lee et al.
(Continued)

FOREIGN PATENT DOCUMENTS

WO       2017/148805 A1      9/2017

OTHER PUBLICATIONS

UV-Sterilization CT Scanner Speeds up Diagnosis of Coronavirus Infection in China, Xinhua, Retrieved from: http://www.xinhuanet.com/english/2020-02/19/c_138798798.htm, Retrieved on: Jan. 6, 2023, pp. 1-2.

*Primary Examiner* — Monzer R Chorbaji
(74) *Attorney, Agent, or Firm* — BakerHostetler

(57) ABSTRACT

Provided are instrument treatment systems, the systems including an insertable portion, the insertable portion being configured for insertion into the bore of a medical imaging system, the insertable portion comprising at least one source of UVC radiation, the insertable portion optionally being constructed to as to be essentially non-interactive with and non-affect by a magnetic field of the medical imaging system. Also provided are related methods of operating the disclosed systems as well as methods of sanitizing the
(Continued)

internal bore of a medical imaging system, such as a magnetic resonance system.

30 Claims, 19 Drawing Sheets

(51) Int. Cl.

| | |
|---|---|
| *A61L 2/24* | (2006.01) |
| *A61N 5/00* | (2006.01) |
| *B08B 1/14* | (2024.01) |
| *B08B 7/00* | (2006.01) |
| *G01J 1/42* | (2006.01) |
| *G01N 21/00* | (2006.01) |
| *G01N 23/00* | (2006.01) |
| *A61L 103/15* | (2026.01) |

(52) U.S. Cl.

CPC ........... *G01J 1/429* (2013.01); *A61L 2103/15* (2026.01); *A61L 2202/11* (2013.01); *A61L 2202/14* (2013.01); *A61L 2202/16* (2013.01); *A61L 2202/17* (2013.01)

(58) Field of Classification Search

USPC ........ 250/491.2, 455.11; 422/28, 24; 15/228

See application file for complete search history.

(56) References Cited

U.S. PATENT DOCUMENTS

| | | | |
|---|---|---|---|
| 2016/0074546 A1* | 3/2016 | Rizzone .................... | A61L 2/10 |
| | | | 250/455.11 |
| 2018/0339073 A1 | 11/2018 | Clynne et al. | |

\* cited by examiner

UVC Source

UVC Sensor

Reflective Surface

Design Criteria

* "MRI Safe"

* Function in MRI Environment

* Efficient Disinfection of Entire Bore and Patient Table

* Ease of Use

- Device "MRI Safe"
- UVC Source and Electronics Function in MRI Scanner
- Easy Setup and Operation Detachable
Cleaning Device Attached
Cleaning
Strip

SYSTEMS AND METHODS FOR ULTRAVIOLET INTRA-BORE TREATMENT OF MEDICAL IMAGING SYSTEMS

RELATED APPLICATIONS

The present application is the National Stage Application of International Patent Application No. PCT/US2021/035935, filed Jun. 4, 2021; which claims priority to and the benefit of U.S. patent application No. 63/035,202, "Systems and Methods for Ultraviolet Intra-Bore Treatment of Medical Imaging Systems" (filed Jun. 5, 2020), the disclosures of which are incorporated herein by reference in their entireties for any and all purposes.

TECHNICAL FIELD

The present disclosure relates to the field of ultraviolet-based disinfection systems.

BACKGROUND

With the emergence and spread of COVID-19, renewed emphasis has been placed on disinfecting contaminated surfaces especially in the medical environment. Numerous bacterial and viral diseases and infections are spread between hosts as humans and animals come into contact with non-disinfected surfaces. Effective and efficient disinfection methods can thus significantly decrease the spread of these pathogens mitigating infection progression and improving overall population health.

A major challenge faced in the medical space is the disinfection of large medical equipment, especially imaging systems which are in constant use and highly technical. One medical system that is a significant challenge to disinfect is the MRI unit, due to the strong magnetic field and space constraints imposed by the bore geometry and size.

The existence of a 1.5 Tesla or greater magnetic field significantly limits the methods that can be used to disinfect the system while the bore size and geometry is a constraint on ease of access. Disinfecting the MRI scanner bore is paramount to mitigating the spread of pathogens due to the substantial time the patient spends in the bore, the close contact between the patient and the bore, and continuous patient turnover, all of which increase the probability of cross-contamination.

Current methods of MRI bore disinfection include the use of harsh chemicals manually applied to the bore's inner surface by an MRI technician. This method is ineffective and time-consuming and is virtually impossible to consistently perform between patients due to scheduling constraints and the MRI technician's patient responsibilities. In addition, the harsh chemicals used can leave behind a residue and noxious fumes that can affect some patients.

Presently, no UVC disinfection system/method exists that can function within the bore of MRI scanners because of the unique challenges this space poses.

SUMMARY

The disclosed technology addresses the shortfalls of the present manual method by eliminating the use of harsh chemicals, minimizing the MRI technician involvement, and providing the capability to rapidly and effectively disinfect the MRI bore between patients. Furthermore, it provides a cost-effective and safe alternative to the existing manual method of MRI disinfection.

It should be understood that although MR systems are used to illustrate the disclosed technology, the disclosed technology is not limited to use with MR systems, as the disclosed technology can be used with essentially any medical imaging system. Further, it should be understood that although the disclosed technology is described as treating the bore(s) of medical imaging systems, the disclosed technology can also treat the patient table associated with a given medical system. Such treatment can include simultaneously treating the table and the bore; a table and bore can also be treated separately/sequentially.

As an example, a system according to the present disclosure can be operated so as to treat the bore of a medical imaging system, and then operated to treat a patient table associate with the system. The bore and table treatments can each be performed by separate sets of instructions. A system according to the present disclosure can also be configured to have two or more states (e.g., a state in which UVC radiation is directed in a first direction, and a state in which UVC radiation is directed in a second direction), which allows a user to direct UVC radiation to a specific location or locations.

Ultraviolet germicidal irradiation is a disinfection method that uses short-wavelength ultraviolet light in the range of 100 nanometers to 280 nanometers (UVC) to inactivate microorganisms leaving them unable to infect host cells halting the infection process. UVC works at the cellular level by destroying nucleic acids disrupting DNA and RNA synthesis. Unlike chemical disinfection, ultraviolet germicidal irradiation leaves no residue or corrosive material behind nor does it generate any noxious odors. Also, by using non-chemical means to control pathogens, the concern of increased chemical resistant bacteria or viruses is mitigated.

In meeting the disclosed challenges, the present disclosure first provides an instrument treatment system, comprising: an insertable portion, the insertable portion being configured for insertion into the bore of a medical imaging system, the insertable portion comprising at least one source of UVC radiation, the insertable portion optionally being constructed to as to be essentially non-interactive with and non-affect by a magnetic field of the medical imaging system.

Also provided are methods, the methods comprising operating a system according to the present disclosure (e.g., according to any one of Aspects 1-29) so as to eliminate an infective microorganism and/or spore from the bore of the medical imaging system.

Further provided are methods, comprising: effecting insertion of at least one source of UVC radiation into the bore of a medical imaging system; the at least one source of UVC radiation being essentially non-interactive with a magnetic field of the medical imaging system, operating the at least one source of UVC radiation so as to eliminate an infective microorganism and/or spore from at least a portion of the bore of the medical imaging system.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various aspects discussed in the present document. In the drawings.

DETAILED DESCRIPTION OF ILLUSTRATIVE EMBODIMENTS

Figure 1:
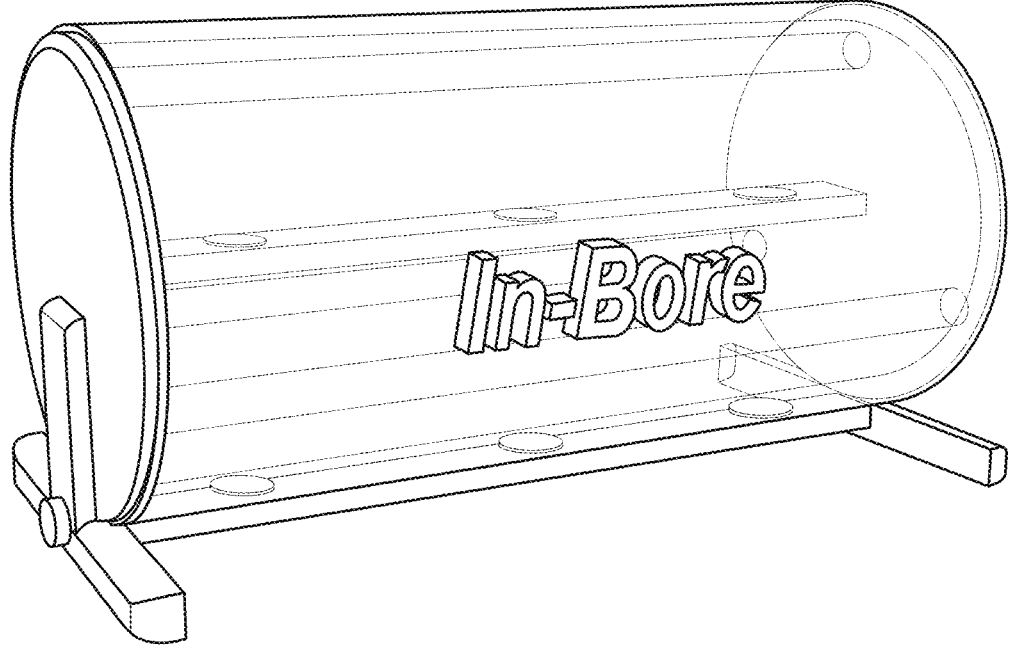
FIG. 1 provides an illustration of the disclosed technology.

The present disclosure may be understood more readily by reference to the following detailed description of desired embodiments and the examples included therein.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing. All publications, patent applications, patents and other references mentioned herein are incorporated by reference in their entirety. The materials, methods, and examples disclosed herein are illustrative only and not intended to be limiting.

The singular forms "a," "an," and "the" include plural referents unless the context clearly dictates otherwise.

As used in the specification and in the claims, the term "comprising" may include the embodiments "consisting of" and "consisting essentially of" The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any impurities that might result therefrom, and excludes other ingredients/steps.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

Unless indicated to the contrary, the numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently of the endpoints, 2 grams and 10 grams, and all the intermediate values). The endpoints of the ranges and any values disclosed herein are not limited to the precise range or value; they are sufficiently imprecise to include values approximating these ranges and/or values.

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. In at least some instances, the approximating language may correspond to the precision of an instrument for measuring the value. The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4. Further, the term "comprising" should be understood as having its open-ended meaning of "including," but the term also includes the closed meaning of the term "consisting." For example, a composition that comprises components A and B may be a composition that includes A, B, and other components, but may also be a composition made of A and B only. Any documents cited herein are incorporated by reference in their entireties for any and all purposes.

FIGURES

The attached figures are illustrative only and do not limit the scope of the present disclosure or the appended claims. Any dimensions given in the figures are illustrative only and are not limiting or required.

FIG. 1 provides an illustration of the disclosed technology. As shown, an in-bore device can include an insertable portion that includes at least one UVC source. A UVC source can be disposed within an enclosure, which enclosure can be essentially transparent to UVC radiation. A device can also include stands, struts, or other features that maintain the device in an upright position and reduce or even eliminate tipping over or rotation.

Figure 2:
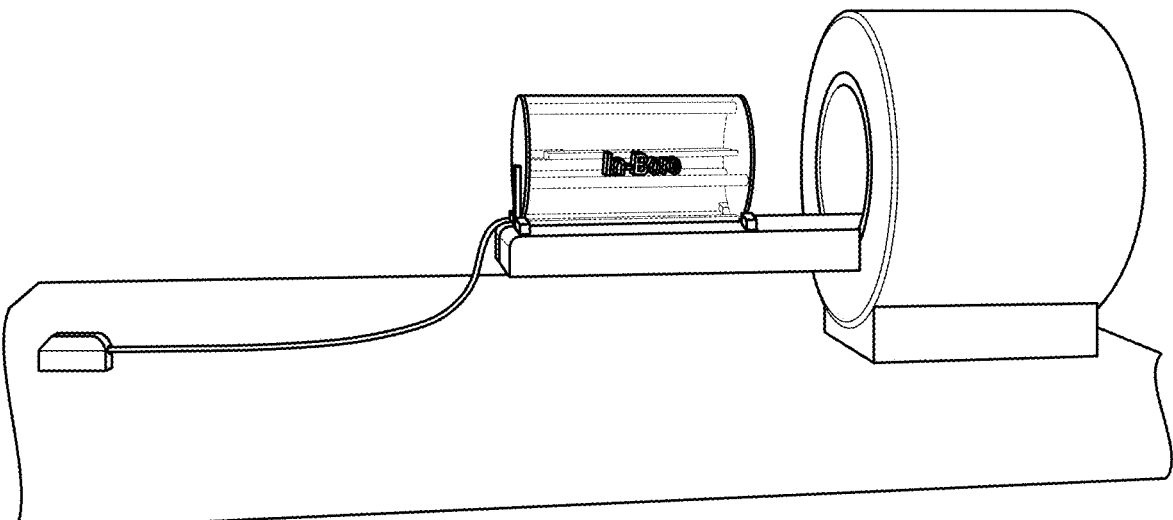
FIG. 2 provides an illustration of the disclosed technology, showing the technology in relation to the bore of an example MR device.

FIG. 2 provides an illustration of the disclosed technology, showing the technology in relation to the bore of an example MR device. As shown, the in-bore device can be of a length that is less than, equal to, or even longer than the length of the bore into which the device is inserted. An in-bore device can be of a length that is less than the length of the bore into which the device is inserted, and the device can be moved along the length of the bore while operating so as to disinfect the interior surface of the bore in an ongoing or incremental fashion.

An in-bore device can, e.g., fit into or otherwise engage with the head coil of an imaging unit, such as an MRI unit. An in-bore device can also engage with the patient table of an imaging unit, such as an MRI unit. In this way, the in-bore device can be translated within the bore of the imaging unit. Mounting brackets, coil connectors, and other such components can be used to engage an in-bore device with a patient table. An in-bore device can also be translated within the inner bore of the imaging system by its own dedicated table or other moveable carrier.

An in-bore unit can, in some embodiments, be integrable with the imaging unit. As one example, the in-bore unit can be configured such that information collected by the in-bore unit (e.g., radiation and other data detected by the sensors of the in-bore unit) is provided to the user via the user interface of the imaging system. In some such embodiments, information collected by the in-bore device is communicated directly through the componentry of the imaging system. This is not a requirement, however, as an in-bore unit can also be in connection with a user interface that is separate from the user interface of the imaging system; in some embodiments, data collected by the in-bore system is not communicated through the componentry of the imaging system. In some embodiments, the in-bore device can be integrable to the source code of the imaging system.

Figure 3:
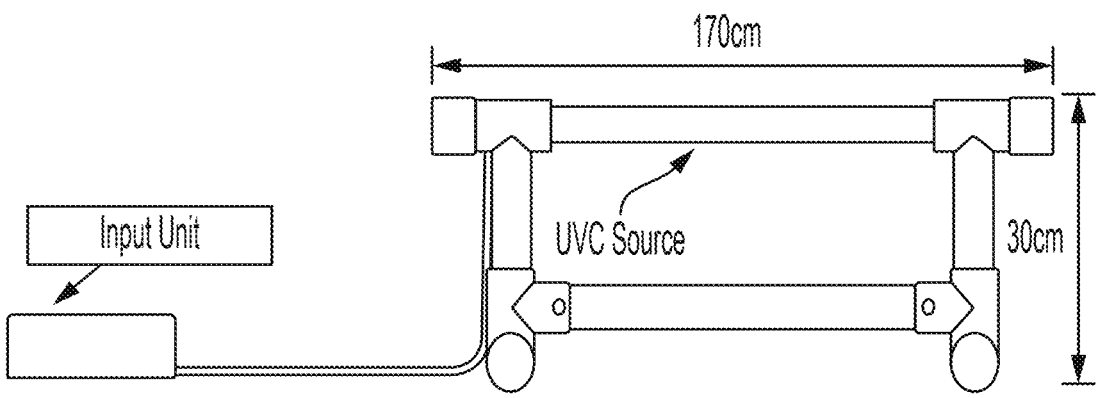
FIG. 3 provides an illustration of an example embodiment of the disclosed technology, with example (non-limiting) dimensions shown.

FIG. 3 provides an illustration of an example embodiment of the disclosed technology, with example (non-limiting) dimensions shown. As shown, a device can include a control unit that is connected to the UVC source, but the control is not itself physically incorporated into the portion of the device that is inserted into the bore. The control can be connected (e.g., via a shielded wire) to the UVC source such that the UVC source enters the bore.

Figure 4:
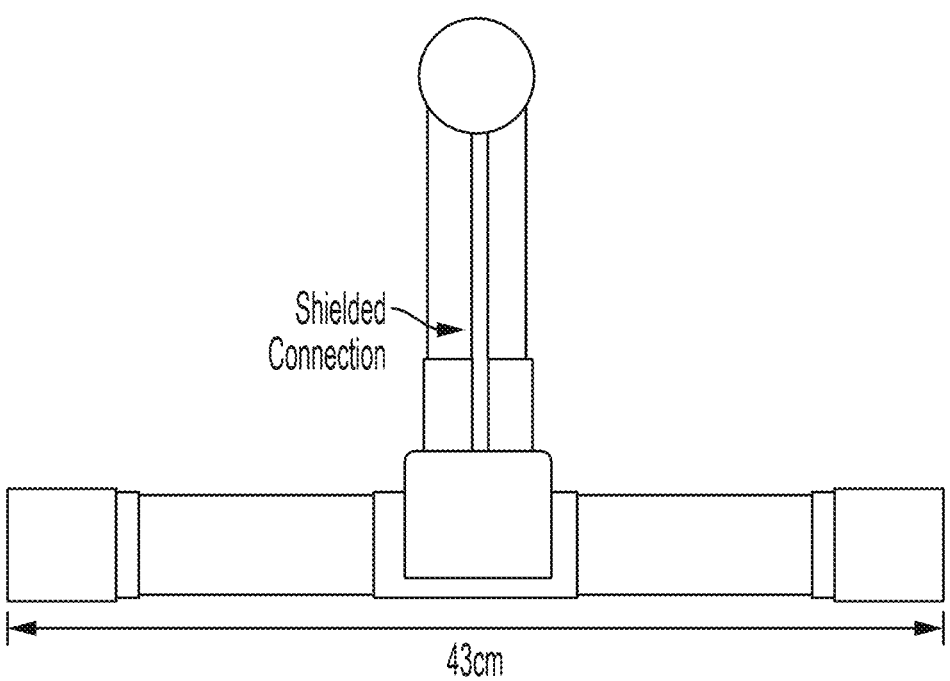
FIG. 4 provides a front view of the embodiment of FIG. 4.

FIG. 4 provides a front view of the embodiment of FIG. 4. As shown, the device can include a shielded connection between an input unit (not labeled) and the UVC source; an input unit can provide power, control, or both to the UVC source.

Figure 5:
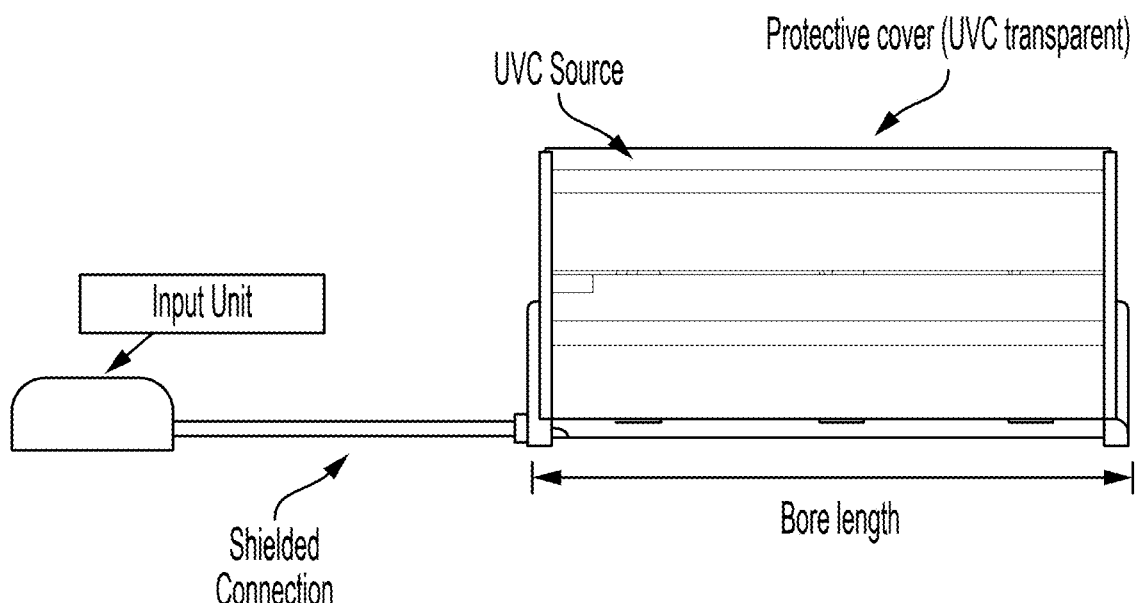
FIG. 5 provides an illustration of an example alternative embodiment of the disclosed technology—this embodiment can be used for bearing treatment while the device is stationary, and device measurements and number of UVC sources used are determined by the dimensions of the MRI bore and level of disinfection required.

FIG. 5 provides an illustration of an example alternative embodiment of the disclosed technology—this disinfection system type can be used for bore treatment while the device is stationary, and device measurements and number of UVC sources used are determined by the dimensions of the MRI bore and level of disinfection required. As shown, a system can include a plurality of UVC sources. The insertable portion of the system can be of a length that is the same as the length of the bore into which the insertable portion is inserted, but this is not a requirement.

Figure 6:
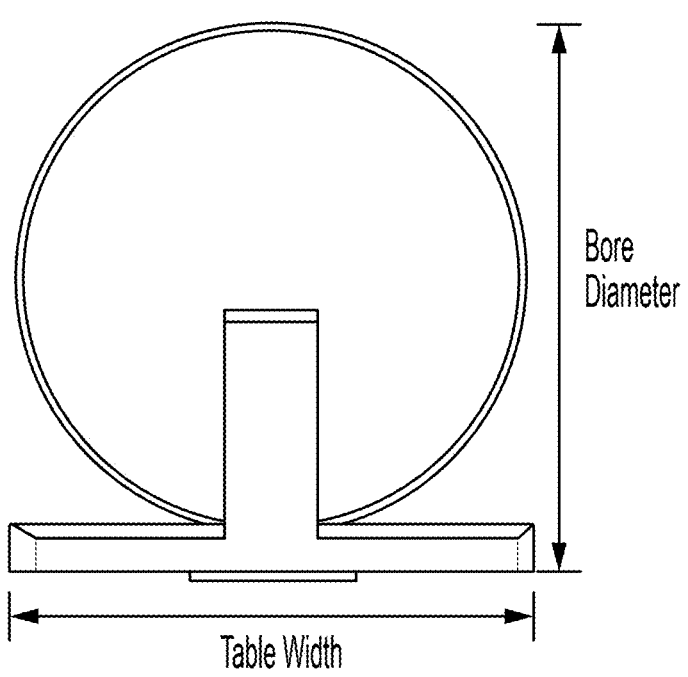
FIG. 6 provides an end view of the embodiment of FIG. 5.

FIG. 6 provides an end view of the embodiment of FIG. 5.

Figure 7:
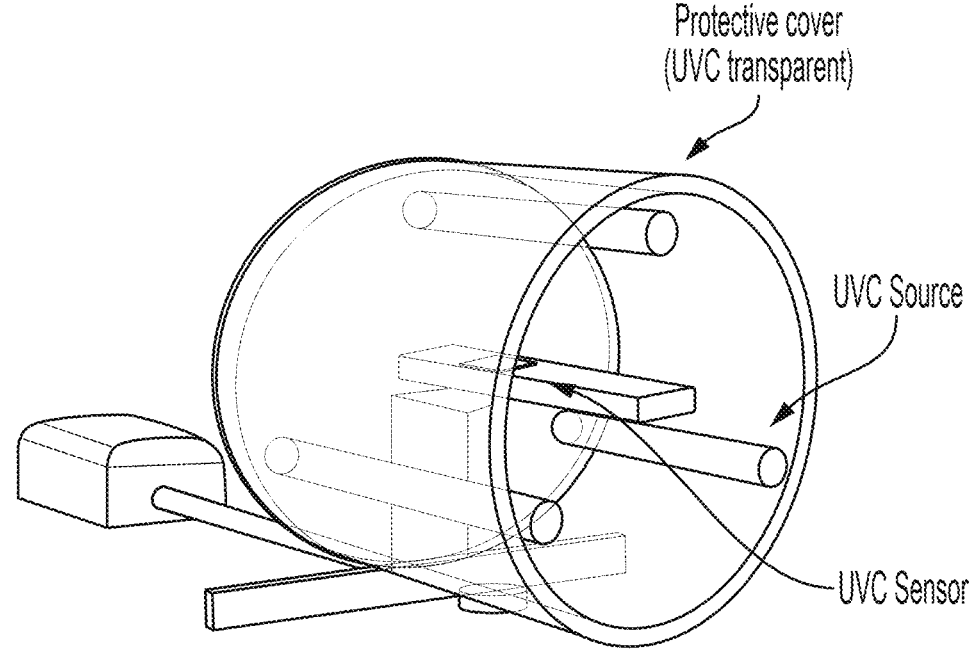
FIG. 7 provides a cross-sectional view of the embodiment of FIG. 5.

FIG. 7 provides a cross-sectional view of the embodiment of FIG. 5. As shown, a device can include multiple UVC sources. A device can also include one or more UVC sensors. Such sensors can be used to monitor device performance and can even be used as part of a control feature, whereby the system is operated in response to one or more signals (e.g., intensity) collected by the one or more UVC sensors. As shown, a device can include a protective cover, which cover can be transparent (or essentially transparent) to UVC radiation.

Figure 8:
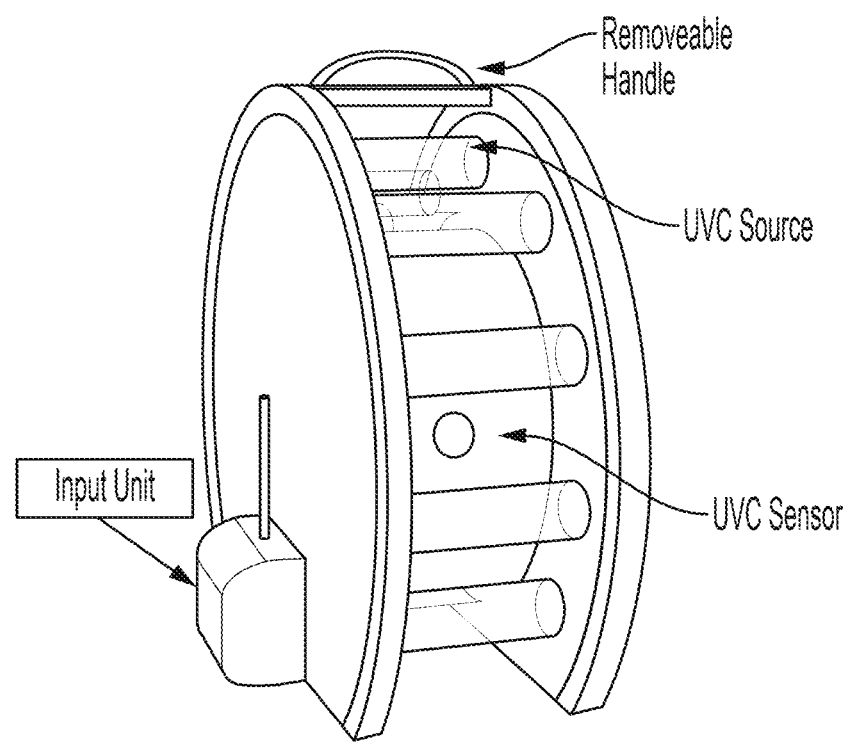
FIG. 8 provides an exemplary embodiment designed for rapid bore treatment while the device is moving so as to traverse the MRI bore—the device height and number of UVC sources can be determined by the bore diameter.

FIG. 8 provides an exemplary embodiment designed for rapid bore treatment while the device is moving so as to traverse the MRI bore—the device height and number of UVC sources can be determined by the bore diameter. As shown, UVC sources can be arrayed in a circumferential fashion. A device can include a handle (which can be removable). A device can also include one or more UVC sensors, which sensors can be part of a control mechanism. As shown, an input unit (which can provide power, control, or both to the UVC source) can be attached to the device such that the input unit enters the bore of the MRI when the device is inserted into the MRI. Data collected by a device according to the present disclosure (and/or the settings used to control such a device) can be archived on the device, on a scanner, in the cloud, or on another storage medium or device. In this way, data and/or settings can be stored and even recalled for future use. Data and settings can also be used to validate device operation, as a user can, for example, determine whether the same given set of settings will, over time, give rise to the same device performance. This can allow a user to monitor the health of a given device; if the same settings used over time do not always result in the same performance (as measured by collected data), a user can monitor device function and determine when device maintenance may be warranted.

Figure 9:
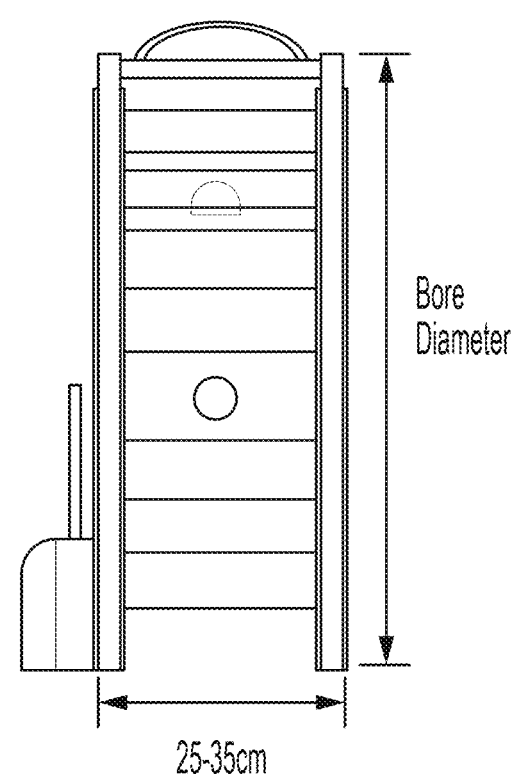
FIG. 9 provides a side view of the embodiment of FIG. 8.

FIG. 9 provides a side view of the embodiment of FIG. 8, with an example, non-limiting dimension. A device can be placed at a first position within an MRI bore and then operated so as to disinfect a first region of the MRI bore that surrounds the device when the device is located at that first position. The device can be then be placed at a second position within the MRI bore, and the device then operated to disinfect a region of the MRI bore that surrounds the device when the device is located at that second position.

Figure 10:
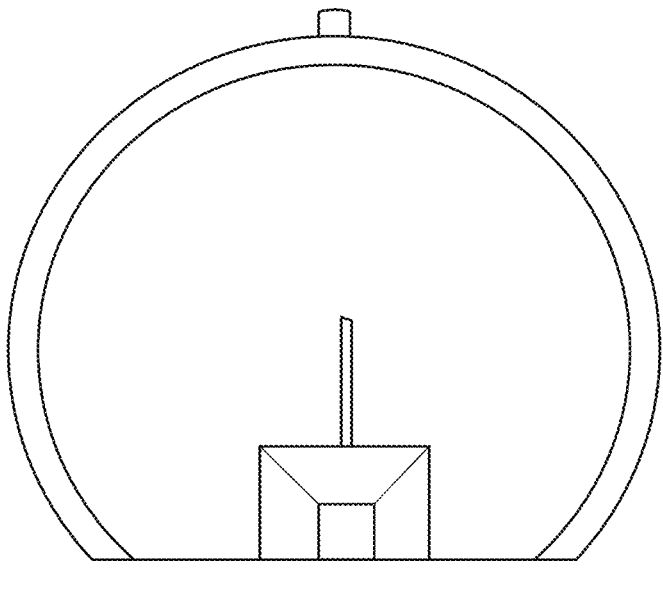
FIG. 10 provides an end view of the embodiment of FIG. 9.

FIG. 10 provides an end view of the embodiment of FIG. 9, showing the input unit. An input unit can have wired and/or wireless connections to the UVC source.

Figure 11:
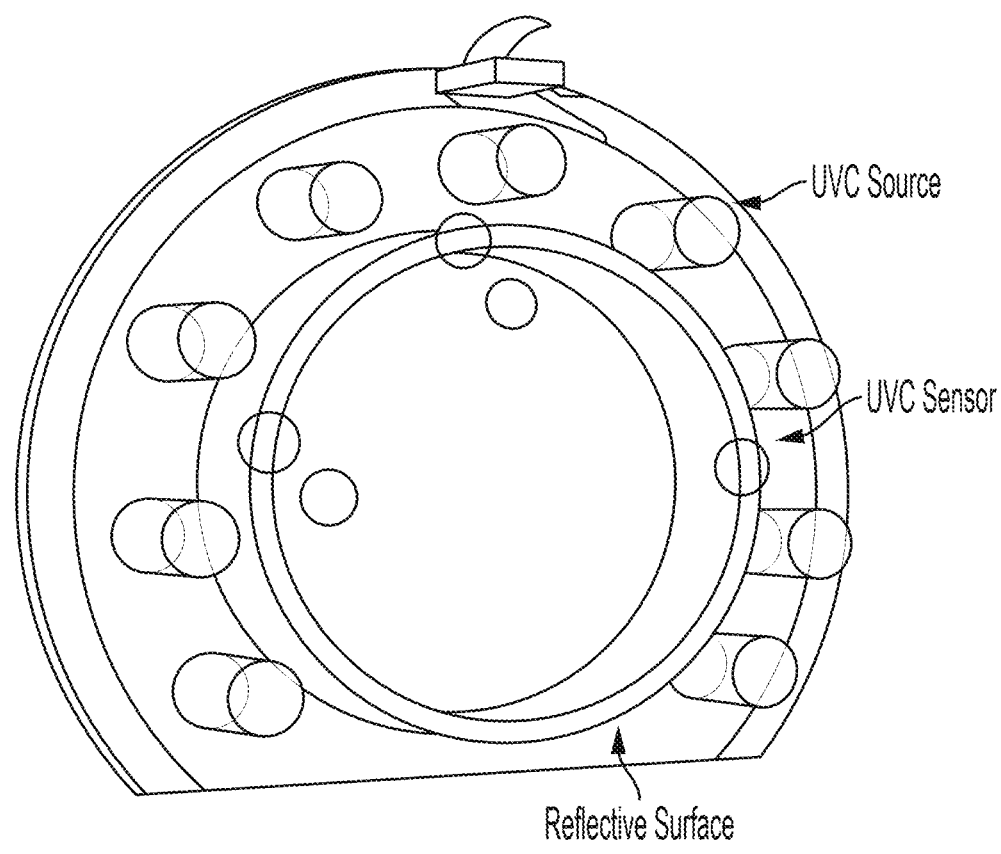
FIG. 11 provides a cross-sectional view of the embodiment of FIG. 8.

FIG. 11 provides a cross-sectional view of the embodiment of FIG. 8. As shown, a device can include a reflective surface, which reflective surface can be of a material that reflects UVC radiation. In this way, radiation that would otherwise initially be directed inwardly (i.e., away from the inner surface of the MRI bore) can be reflected and then (re)directed outwardly, toward the surface of the bore. Such reflection can allow the device to then operate at a relatively higher efficiency, reducing treatment times, increasing efficacy, and thereby improving throughput.

Figure 12:
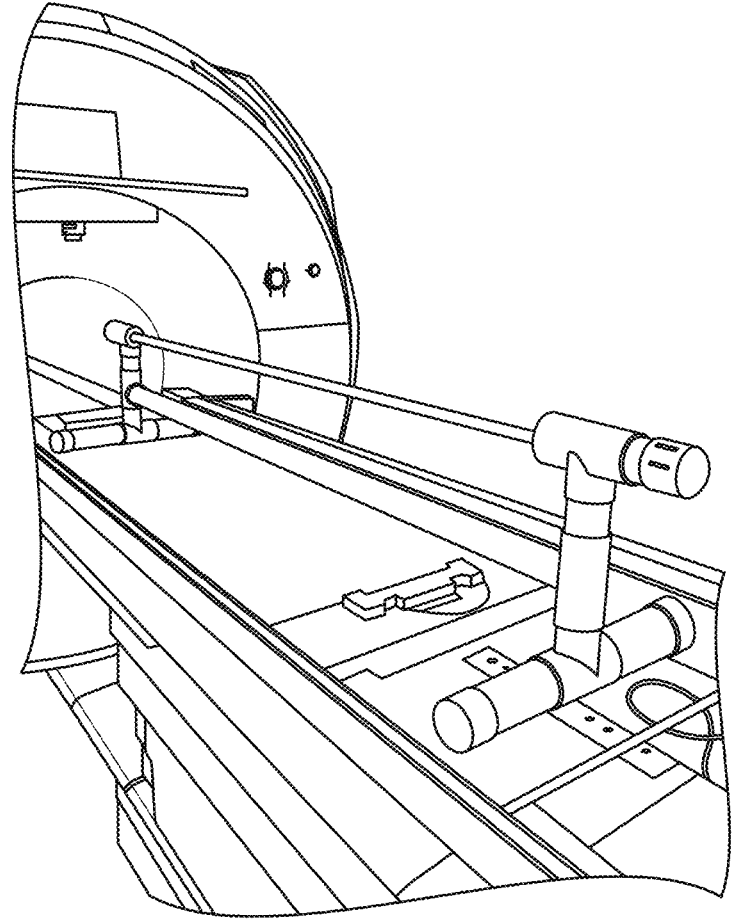
FIG. 12 provides a photo of an exemplary, non-limiting embodiment of the disclosed technology.

FIG. 12 provides a photo of an exemplary, non-limiting embodiment of the disclosed technology. This non-limiting image provide a sense of the scale that a device can have.

Figure 13:
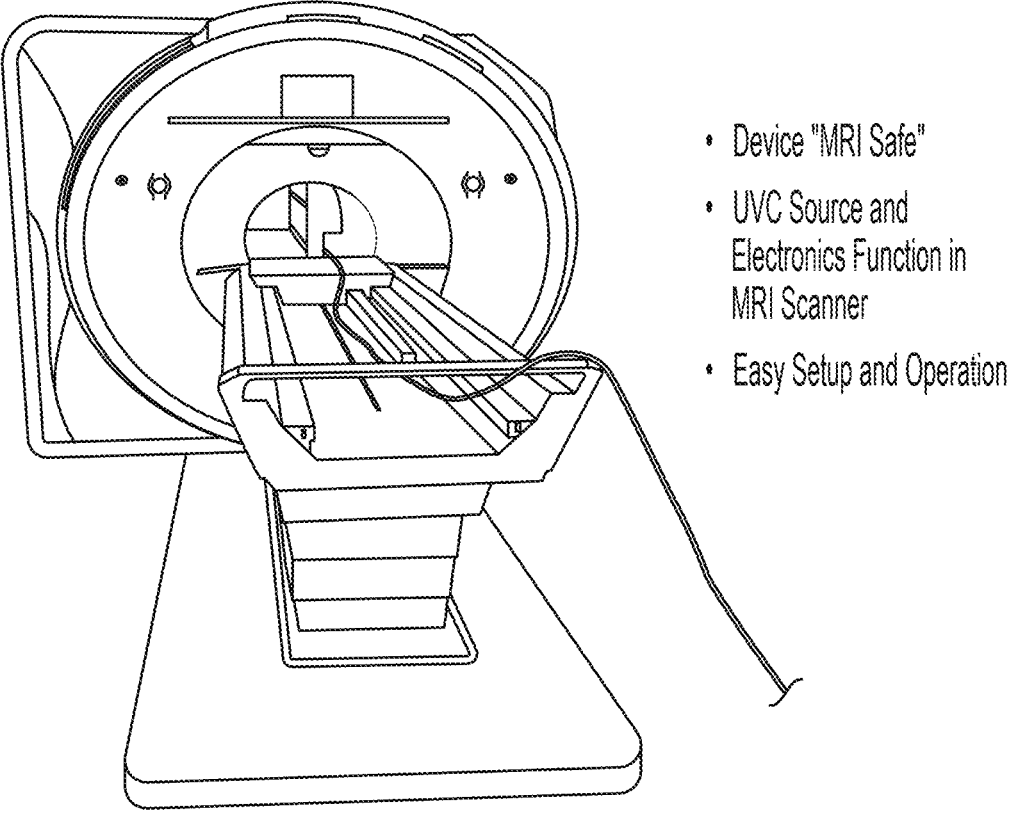
FIG. 13 provides a photo of an exemplary, non-limiting embodiment of the disclosed technology.

FIG. 13 provides a photo of an exemplary, non-limiting embodiment of the disclosed technology. This non-limiting image provide a sense of the scale that a device can have.

Figure 14:
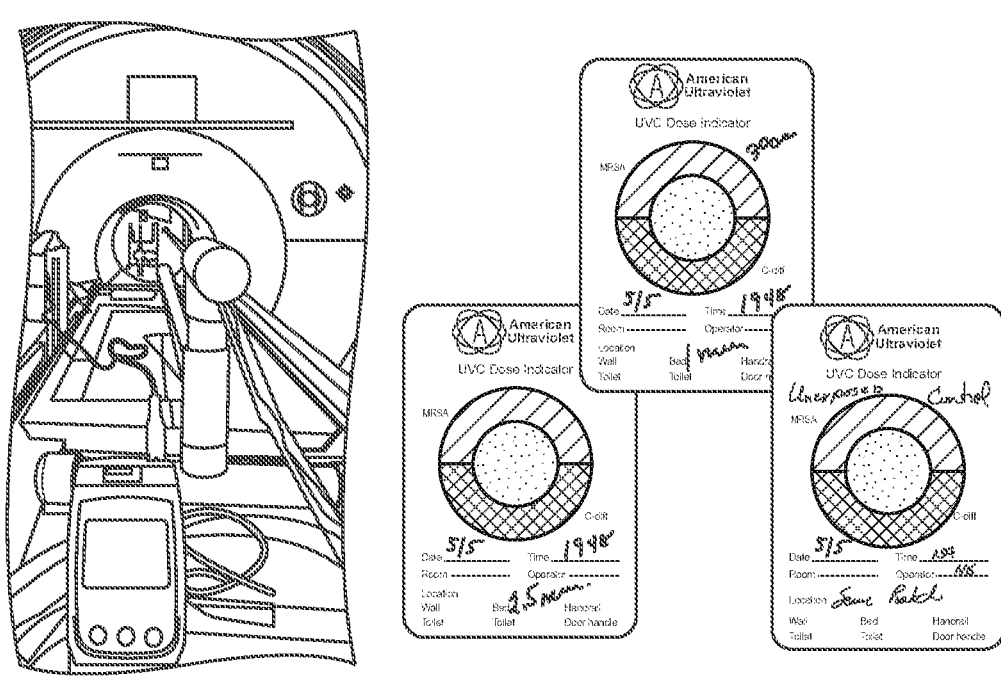
FIG. 14 provides an exemplary, non-limiting illustration of the disinfection capabilities of an exemplary embodiment of the disclosed technology.

FIG. 14 provides an exemplary, non-limiting illustration of the disinfection capabilities of an exemplary embodiment of the disclosed technology. As shown by the UVC dose indicator badges, an example (non-limiting) embodiment of the disclosed technology achieved a UVC dose sufficient to eliminate MRSA within about 1 minute, and sufficient to eliminate *C. diff* within about 2.5 minutes.

Figure 15:
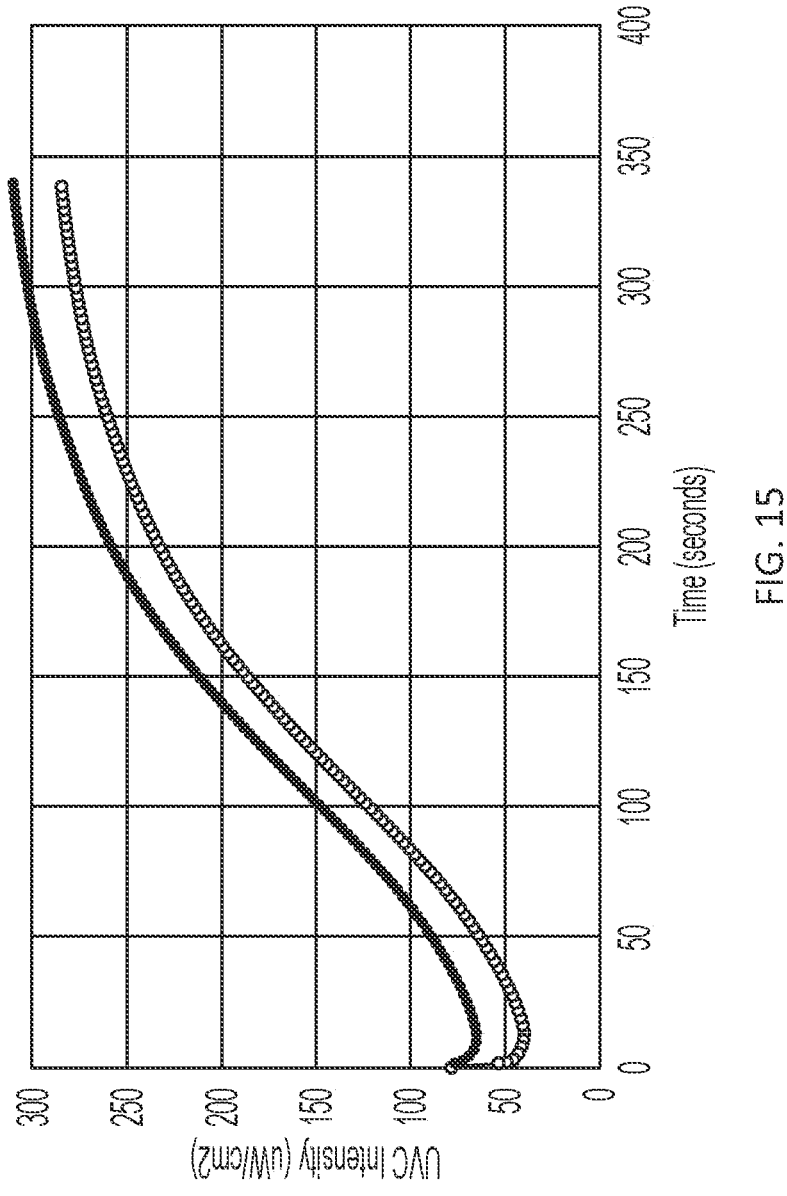
FIG. 15 provides an exemplary curve showing UVC intensity (as a function of time) for an exemplary UVC source.

FIG. 15 provides an exemplary curve showing UVC intensity (as a function of time) for an exemplary UVC source. As shown, the example (non-limiting) source achieved a maximum intensity after operation for about 300-350 seconds.

Figure 16:
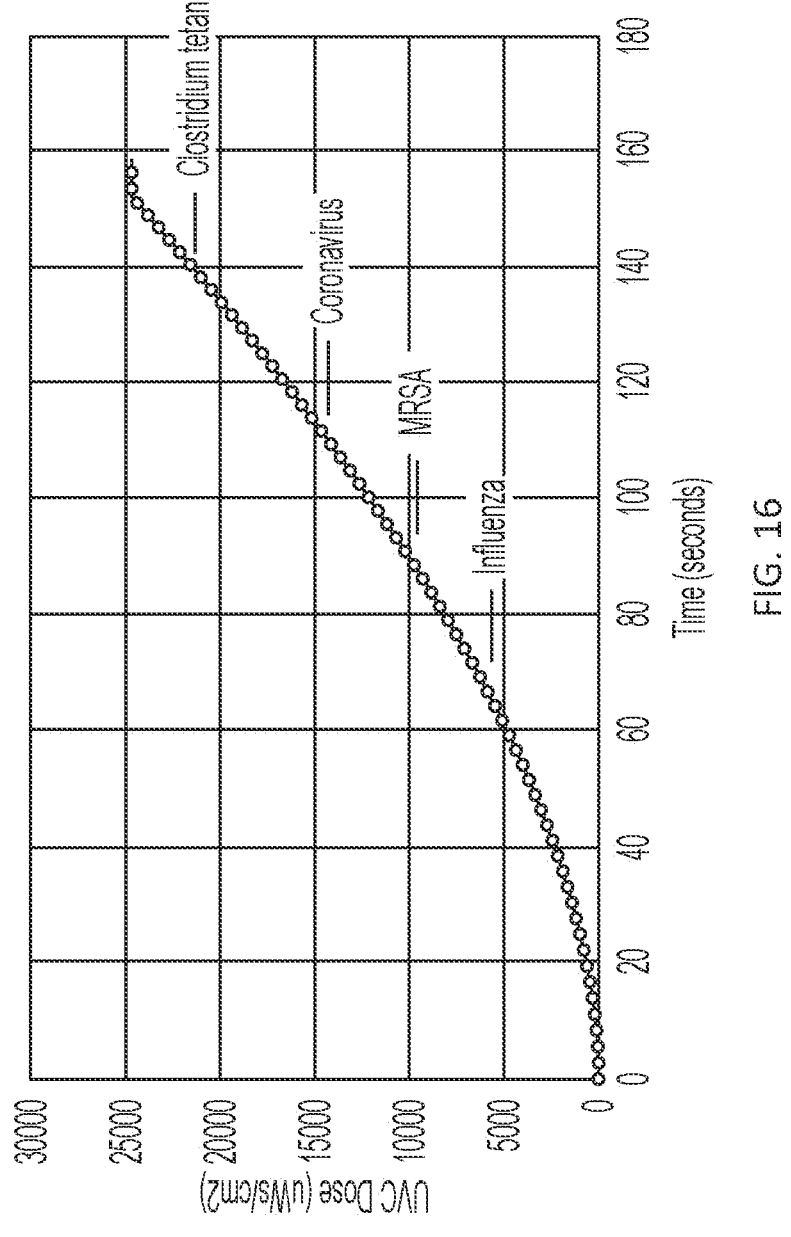
FIG. 16 provides an exemplary curve showing UVC doses effective to eliminate various exemplary pathogens of interest.

FIG. 16 provides an exemplary curve showing UVC dose (as a function of time) effective to eliminate various exemplary pathogens of interest.

Figure 17B:
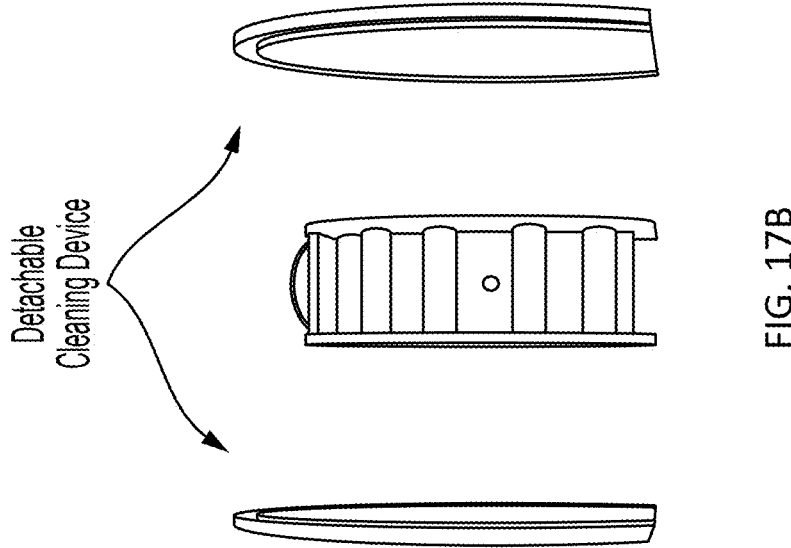
FIGS. 17A-17B provide an alternative embodiment of the disclosed technology. As shown, FIG. 17A provides a view of a component according to the present disclosure that includes attached cleaning strips. (Such strips can be permanently attached but can also be detachable.) FIG. 17B provides a view of a component according to the present disclosure, showing detachable cleaning devices.
Figure 17A:
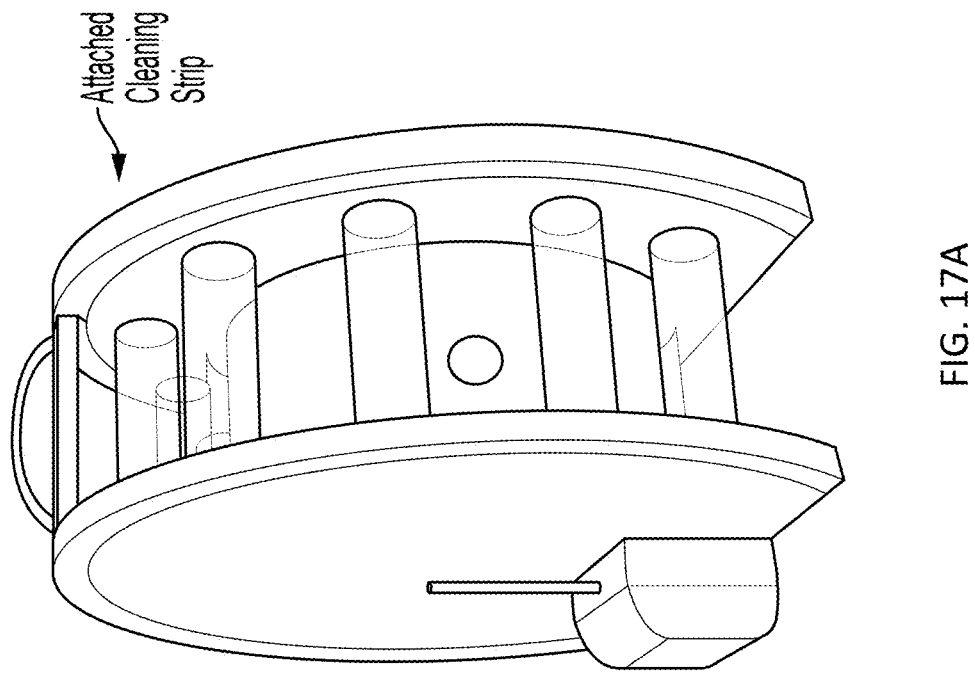

FIGS. 17A-17B provide an alternative embodiment of the disclosed technology. As shown, FIG. 17A provides a view of a component according to the present disclosure that includes attached cleaning strips. (Such strips can be permanently attached but can also be detachable.) FIG. 17B provides a view of a component according to the present disclosure, showing detachable cleaning devices.

As shown in FIG. 17A, an insertable portion can include one or more cleaning strips. Such strips can be configured to contact the interior surface of the bore being treated, i.e., to introduce a cleaning solution and/or to physically remove material that may be deposited on the interior surface of the bore. As but one non-limiting example, such cleaning strips can be used to remove sneeze residue from the interior bore of the imaging unit. A cleaning strip can be spongy or otherwise pervious; such configurations are useful to retain (like a sponge) the cleaning solution. A device can be configured such that one strip (e.g., the strip that first enters the bore) is preloaded with cleaning solution, and another strip (e.g., the strip that second enters the bore) absorbs or wipes the cleaning solution from the surface of the bore. This is not a requirement, as none, one, or both of the cleaning strips can be loaded with cleaning solution. It should be understood that a component according to the present disclosure can include zero, one, or even a plurality of strips; FIGS. 17A and 17B illustrate an example, non-limiting embodiment that includes two strips.

As shown in FIG. 17A, cleaning strips can be attached to the insertable unit. As shown in FIG. 17B, such cleaning strips can be removeable, although this is not a requirement. A cleaning strip can be removeable to allow for replacement, re-loading with cleaning solution, and the like. Cleaning strips can be sized so as to maintain contact around a portion or even the entirety of the circumference of the inner surface of the bore; the dimensions of a given cleaning strip will be determined based on the dimensions of the inner surface of the bore. In addition to being configured to clean the interior bore of the imaging unit, cleaning strips can also be configured to clean the patient table (i.e., the bed on which a patient is disposed during imaging). As with the interior bore, the dimensions of such cleaning strips will be based on the dimensions of the patient table.

Figure 18:
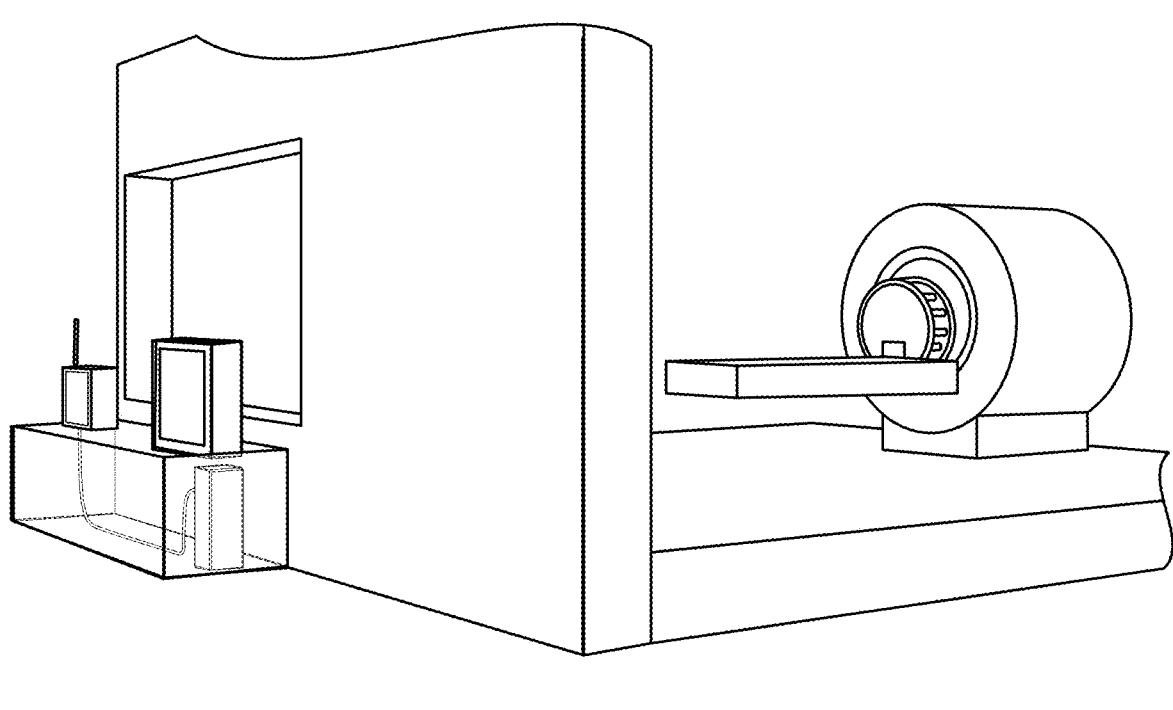
FIG. 18 provides a view of an exemplary system according to the present disclosure. As shown, a system can include a portion that is insertable into the bore of a medical imaging unit (e.g., an MRI system). The system can include a wired or wireless (e.g., Wi-Fi) connection to a user interface and/or control system, which user interface and/or control system can be located in a room or other enclosure separate from the medical imaging unit.

FIG. 18 provides a view of an exemplary system according to the present disclosure. As shown, a system can include a portion that is insertable into the bore of a medical imaging unit (e.g., an MRI system). The system can include a wired or wireless (e.g., Wi-Fi) connection to a user interface and/or control system, which user interface and/or control system can be located in a room or other enclosure separate from the medical imaging unit. As described elsewhere herein, a system according to the present disclosure can be interfaced with a medical imaging system's scanner and/or software.

Figure 19:
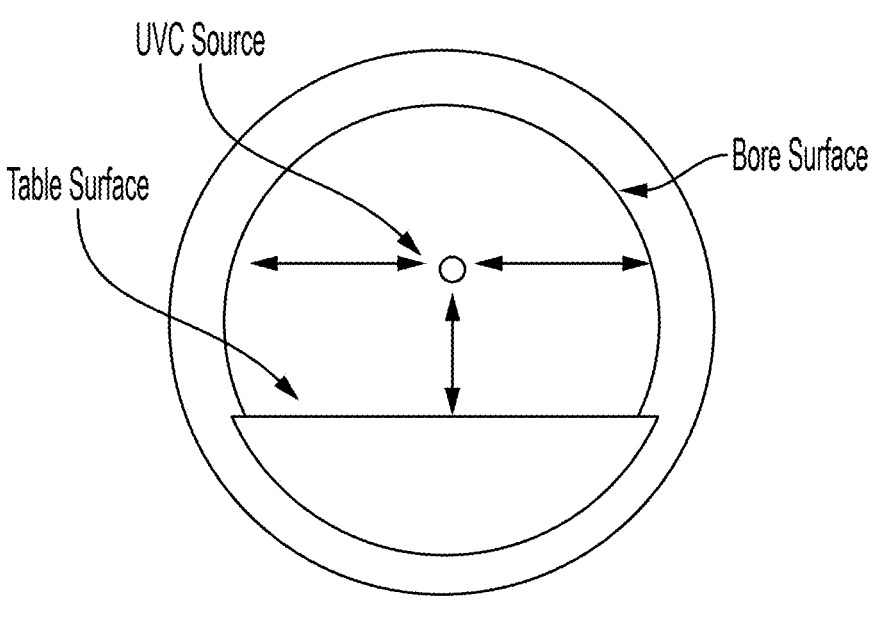
FIG. 19 provides a model-derived single-source model optimized location for minimum exposure time.

FIG. 19 provides a model-derived single-source model optimized location for minimum exposure time. As shown, a single source can deliver UVC radiation to the interior surface of the medical imaging system as well as to the surface of the patient table.

Figure 20:
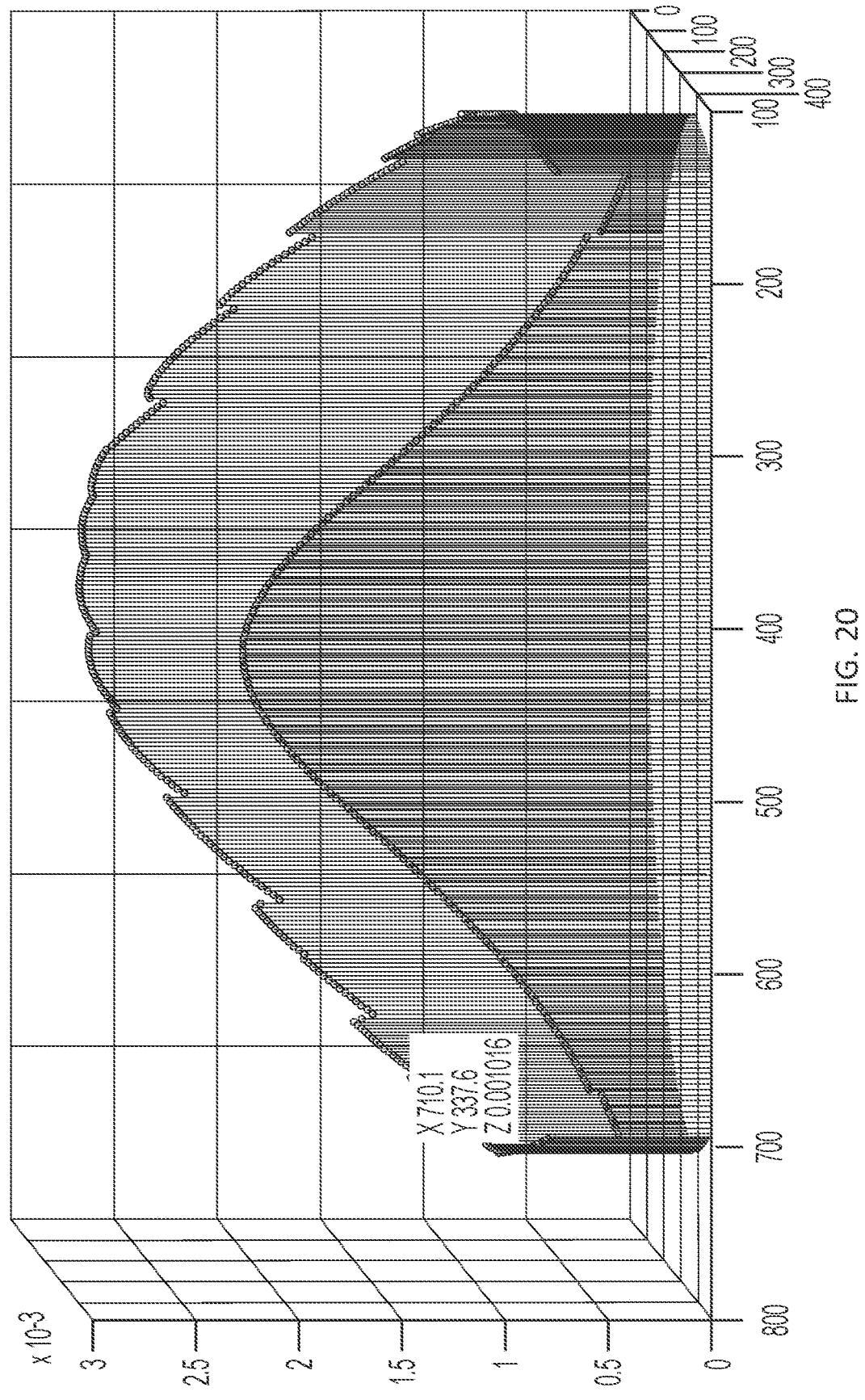
FIG. 20 provides a model-derived single-source histogram of surface intensities.

FIG. 20 provides a model-derived single-source histogram of surface intensities, e.g., from the system shown in FIG. 19.

Figure 21:
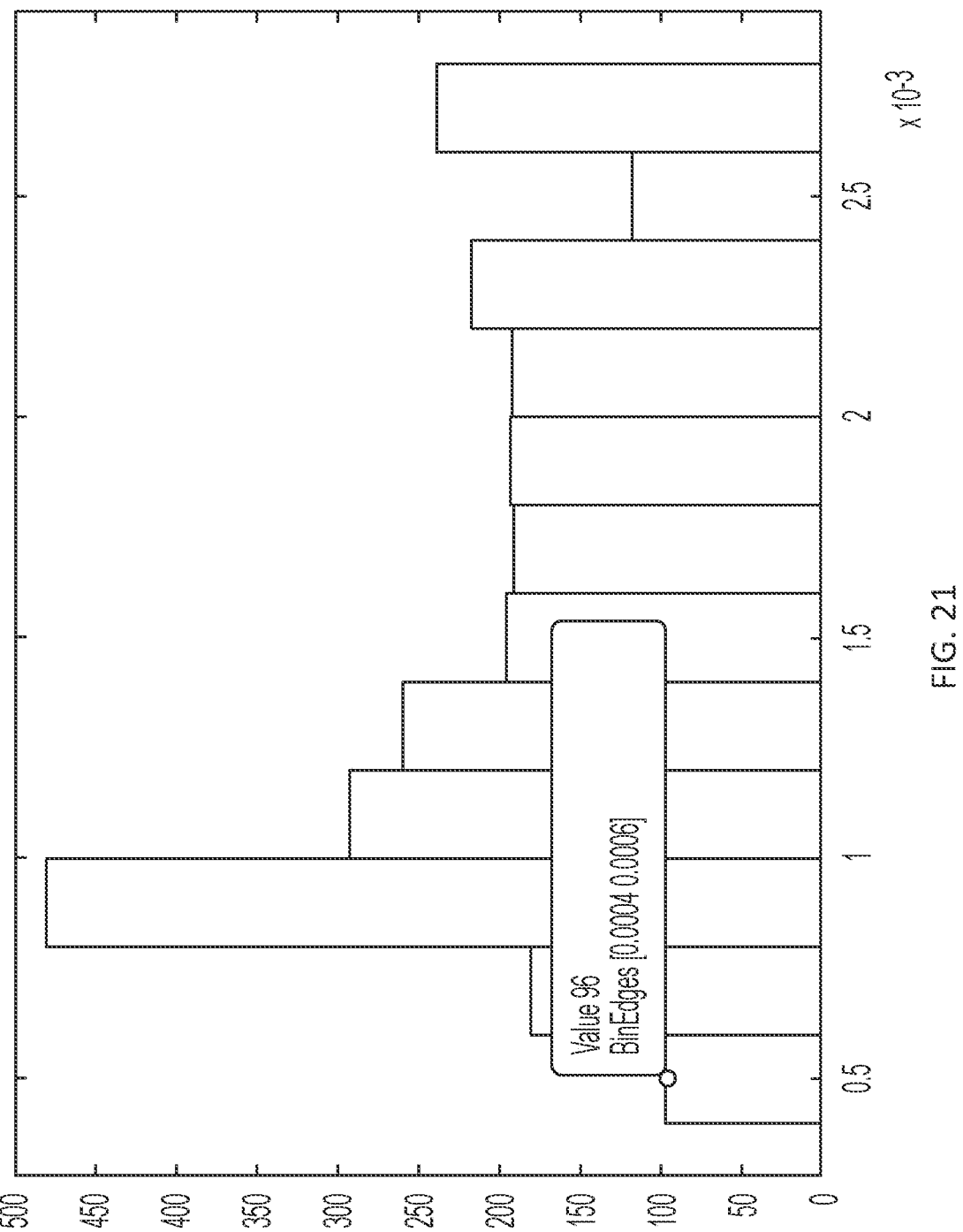
FIG. 21 provides model-derived single-source surface intensities values for bore and patient table.

FIG. 21 provides model-derived single-source surface intensities values for bore and patient table, e.g., from the system shown in FIG. 19.

Figure 22:
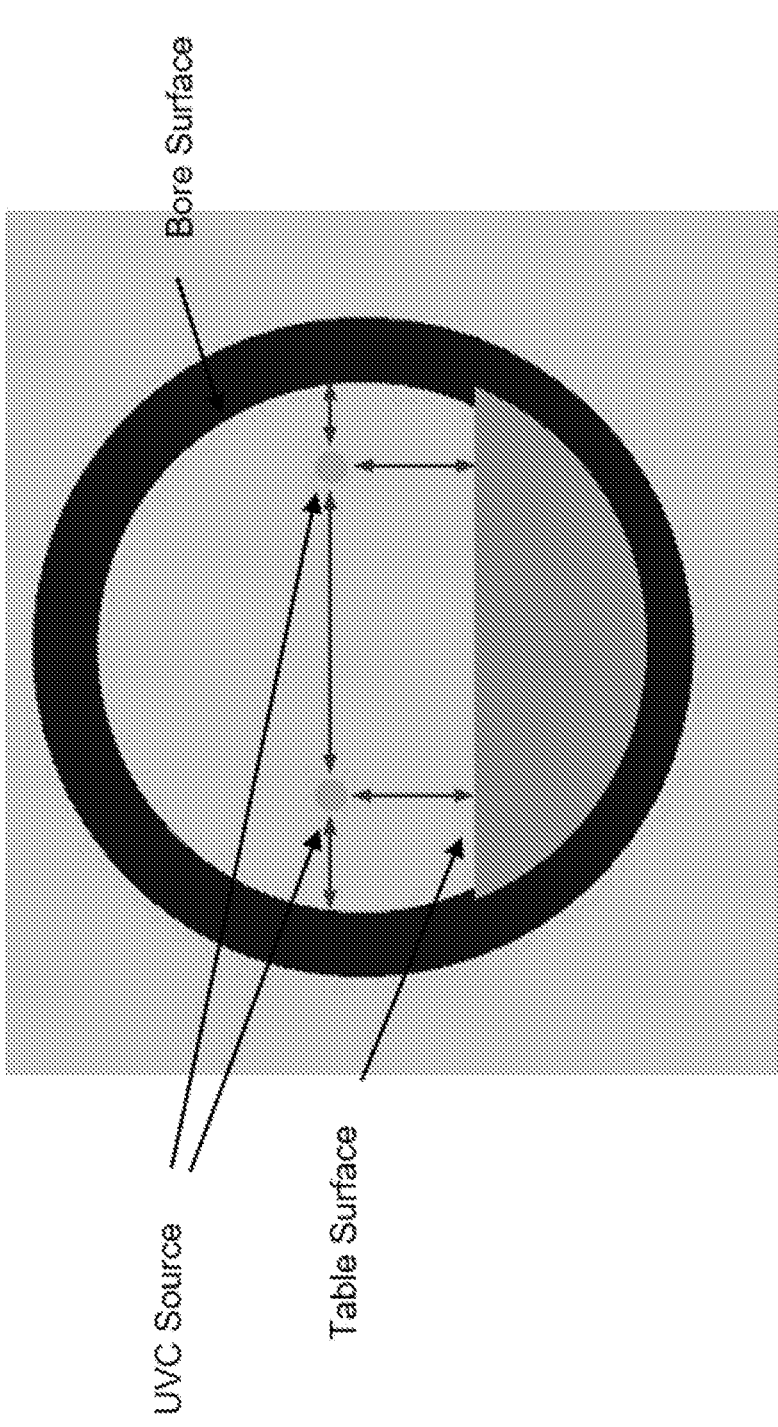
FIG. 22 provides a model-derived dual-source model optimized location for minimum exposure time.

FIG. 22 provides a model-derived dual-source model optimized location for minimum exposure time. As shown, a system can include two UVC sources, spaced apart from one another.

Figure 23:
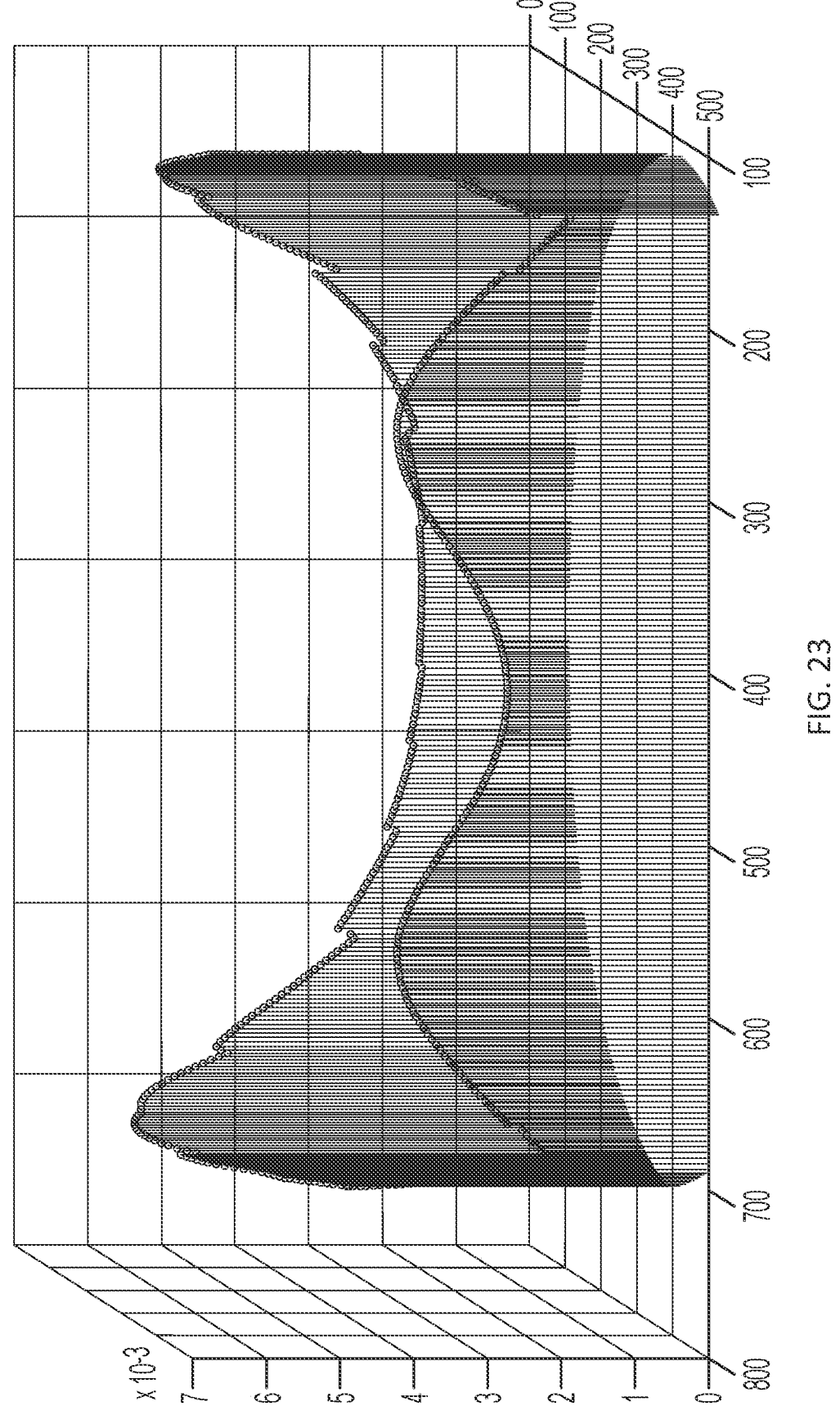
FIG. 23 provides a model derived dual-source histogram of surface intensities.

FIG. 23 provides a model derived dual-source histogram of surface intensities, e.g., from the system shown in FIG. 22.

Figure 24:
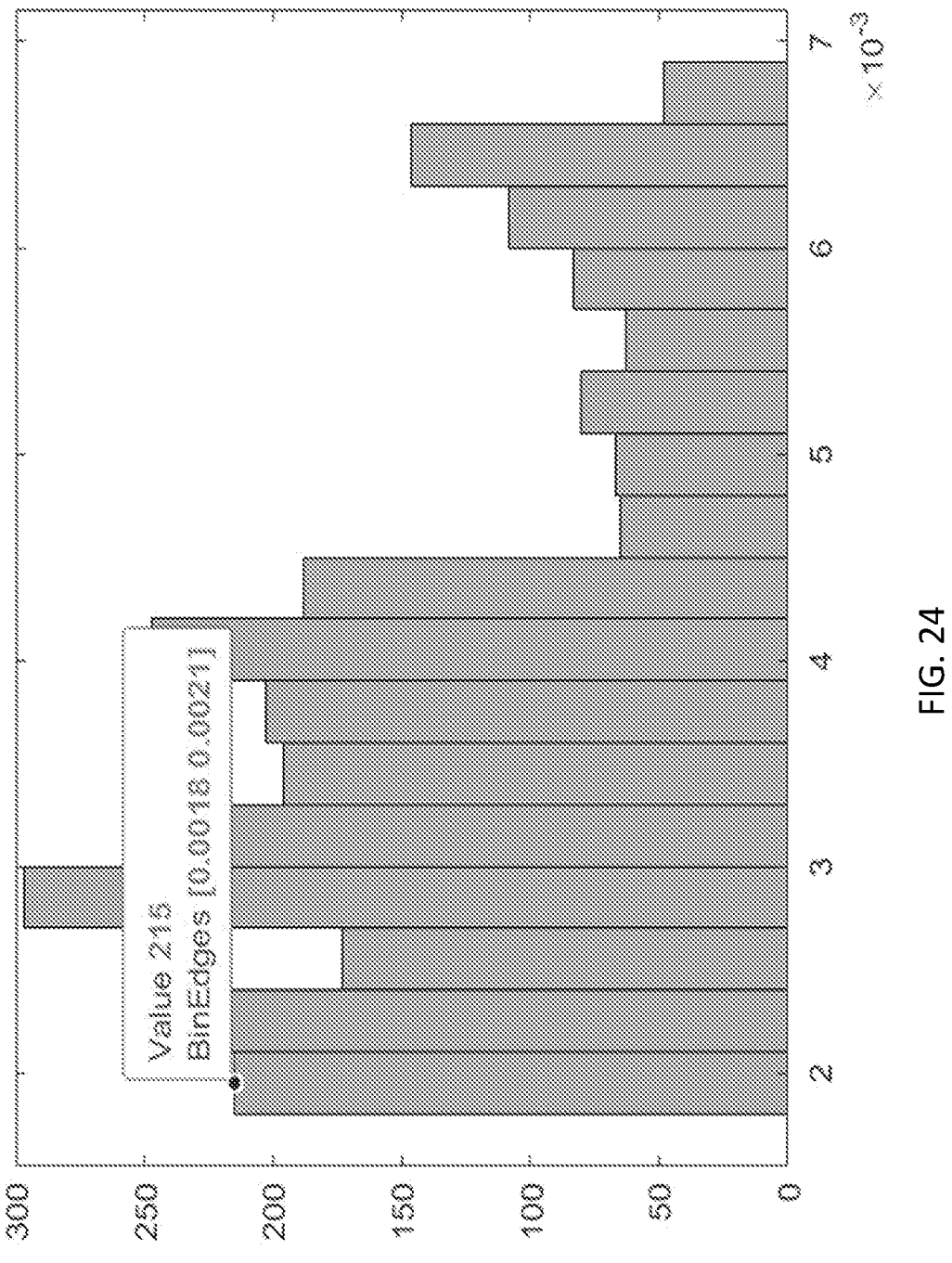
FIG. 24 illustrates model-derived dual source surface intensities values for bore and patient table.

FIG. 24 illustrates model-derived dual source surface intensities values for bore and patient table, e.g., from the system shown in FIG. 22.

FURTHER DESCRIPTION

To meet the described challenges, the described systems can be constructed using non-ferrous components for both the structure and UVC source. As an example, a support structure is fabricated using polyvinyl chloride, a rigid and light-weight non-ferrous plastic. An MRI-safe UVC source was determined by evaluating and testing different source configurations to ascertain which meet the "MRI safe" criteria. For proper and effective operation in the magnet field the electronics to power and control the system are suitably impervious to the field. This can be achieved by designing and/or shielding the electronic components to minimize magnetic field interference. Shielding materials include (but are not limited to) sheet metal, metal screen, and metal foam, to provide but a few examples.

One consideration for disinfection systems is effective disinfection of an MRI bore with minimal MRI personnel involvement. For maximum effectiveness at controlling pathogen spread, disinfection should occur between each patient with little to no disruption to MRI schedule. This requires disinfection of the bore be limited to the time between the conclusion of one patient's scan and the scanner setup for the next patient which is approximately five minutes.

To accomplish disinfection within this time constraint, the disclosed technology can produce an intensity of UVC at the bore surface to disinfect the entire MRI bore with 1-2 minutes of source on-time. In addition, the system is designed for rapid setup and removal with very little personnel involvement and a total time commitment of 2-3 minutes.

The long-felt need for such technology is made clear with the role of MRI expanding in healthcare and scientific research. MRI scanners are being outfitted into operating rooms worldwide and the disinfection of those units will be required to minimize pathogen cross-contamination. As of 2020, there are 11,900 MRI scanners in the United State alone (not including animal and cell imaging spectroscopes) and approximately 40,000 worldwide. Expansion of MRI use into the emergency and operating rooms makes disinfection even more important. Depending on the scheduling of individual MRI's and the defined workflow of the operators, an individual system can see up to twenty-five patients per day. Further, many systems operate on a twenty-four hours a day, seven days a week schedule, requiring that any disinfection be performed within the brief time between patient scans.

In meeting these needs, the disclosed technology utilizes UVC radiation to disinfect the bore of an MRI scanner and potentially other equipment within the MRI suite. It is constructed of MRI safe components for both the structure and UVC source. As but one example, utilizing a 254 nm wavelength emitting MR compatible light source, this instrument can disinfect (to 3 logs) contact surfaces within the MRI bore and table in a time frame that is consistent with current clinical workflows (a goal time to disinfect the bore between patients is approximately 5 minutes). The disclosed technology also requires minimal technician involvement/interaction, and does not interfere with the imaging operation of the scanner.

Example Device

A prototype frame of the device was fabricated using a polyvinyl chloride frame with approximate dimensions of length=170 cm, width=43 cm, and height=30 cm. Polyvinyl chloride was chosen based on its MRI compatible properties and strength versus weight ratio. The frame of the device can be constructed using other materials such as nonmagnetic metals, and nonmagnetic composite materials.

In addition to being MRI compatible, another design criterion is for the material to be impervious to UVC radiation. Importantly, this design can accommodate the breadth of imaging modalities and models used for radiologic imaging including, but not limited to, CT, PET, PET-MR, SPECT scanners.

Example UVC Source and Design

An example was built using a UVC radiation source that emits ultraviolet light at a wavelength of 254 nm wavelength. This wavelength is optimal for maximum absorption resulting in effective neutralization of pathogens. The UVC source for the device was selected by investigating and testing numerous alternatives in order to determine which would function properly within the intense magnetic field present in the MRI bore. In addition, the length of the source (150 cm) and the intensity were chosen to facilitate rapid disinfection of the MRI bore.

The UVC source is physically supported by the device frame which holds the lamp at the iso-center of the bore. This symmetrical placement optimizes the incident angle of the UVC light wave and creates an optimal scenario for uniform treatment of the bore. A device can include several UVC emitting lamps or LEDs, e.g., in a configuration that optimizes distance, effectiveness, and treatment time. A unit can allow single user deployment, activation, and removal including an automated, remote system for introducing the system into the bore and light source activation. The device also allows for storage of the device inside the MRI suite (not the bore) during active scanning.

Device Movement into Bore

The disinfection system can be moved into and out of the MRI bore using the patient table in the manual mode. The procedure is to place the device on the patient table, landmark the device using protocols in place on standard MR scanners, and then activate the patient table by manually pressing the "table in" control located at the front of the MRI bore. The disclosed technology can also, however, interface directly with the MRI software to control the table movement based on feedback from the device. This option will enable "push button" operation to move the device into optimal position within the bore, complete the disinfection cycle based on feedback from sensors positioned within the bore or on the device and move the device out of the bore with an indication of cycle completion generated on the scanner's computer. The device can also use a standalone mechanism to move the device into and out of the bore (separate from table). A device can (but need not) include a feature (e.g., brush, flexible ridge, and the like) or surface that contacts bore surface so as to assist with cleaning of fluids and other substances from the bore surface.

Control Systems

MRI compatible UVC sensors can be placed on the device or the bore to monitor UVC intensity and dosage over time. Data from these sensors can be logged and archived for analysis of UVC source performance and measure the achieved level of disinfection. The UVC sensor system with feedback to control software enables the user to treat according to actual accumulated exposure which can be adjusted depending on pathogen of interest. Sensor feedback also controls device movement by activating the patient table or device locomotion mechanism when treated areas achieve the required dose.

Electrical and Electronics System

Electrical and electronic components are suitably MRI safe and/or MRI compatible, though this is not an absolute requirement. This can be accomplished by selecting components that can function in the MRI environment and/or by using EMI shielding to minimize magnetic field interference.

UVC Radiation

UVC light can be a safety issue for individuals that are not wearing protective gear. Therefore, a device can include UVC blocking devices positioned in a manner that protects the end user and a system can even be automated such that the technician need not enter the room during UVC application. There can be visual, and/or audio feedback in addition to the dosimeter feedback allowing the operator to know UVC is being emitted as well as visual feedback integrated into the software to indicate completion of disinfection cycle and shutdown of the light source.

Construction

As described above, PVC can be used, examples, based on that material's non-magnetic properties, light weight, tensile strength, low cost, and adaptability.

Materials

Materials used as structural supports can be non-magnetic UV-resistant materials, e.g., fluoropolymer materials, or materials covered by fluoropolymers. Alternatively, materials without these UV-resistant properties can be used and covered with highly reflective material. A support frame can include tubular sections, I, or H-beams of plastics of the above properties and/or light non-magnetic metals including high tensile-grade aluminum alloys, and the like. A combination of plastic and non-magnetic frame elements can be used. One can use metal-based constructions; such constructions can be made such that their the segments are electrically isolated, i.e., no closed current path exists.

UVC Sources

Regarding UVC sources, a source suitably has the following characteristics:

1—The device is not paramagnetic, ferromagnetic or does not show paramagnetic or ferromagnetic attraction to the MRI's main magnetic field.

2—The device does not passively interact with the changing magnetic fields present during MRI Imaging. This system is not used in the bore and is designed and evaluated mitigate image degradation.

3—The device does not interact with, or cause damage to, the MR scanner components during start-up or operation of the disinfection cycle. (The foregoing three characteristics can also be used to guide the selection of other components of the disclosed devices/systems.) The strong magnet field present in the MRI suite requires that a disinfection system be "MRI safe" and able to function properly within the field. "MRI safe" dictates that none of the device components in direct contact with the magnet field be constructed of materials that are attracted by the field potentially creating a dangerous projectile.

A variety of UVC sources can be used. Some non-limiting examples include (without limitation): all ranges of traditional UV-biocidal lamps from low to high pressure lamps; excimer lamps and lasers; halved-wavelength blue-laser sources; dye-lasers; high energy xenon lights; and LED sources. Magnetically compatible UVC sources are considered especially suitable; a UVC source that interacts with a magnetic field can be shielded and used in the disclosed technology.

As described elsewhere herein, a number of UVC sources can be used in a given system. As a non-limiting example, from one to six high, or mid power-range, central line-sources, or multiple, lower power-range point-sources can be used, e.g., so as to sufficiently expose all surface areas to be disinfected. The number, type and location of the sources will depend on whether the disinfecting device is of static, or dynamic in nature (i.e., moving through the bore).

Wavelength

Radiation wavelength can be of any wavelength that that effects the structural (e.g., RNA structure, DNA structure) disruption necessary for bacterial and viral elimination. Exemplary wavelengths include, e.g., 254 nm; emission centered around 222 and 265 nm (the biocidal "kill-peaks" of the UV-C spectrum). A suitable range can be from about 200 to about 280 nm, e.g., from 207 to 280 nm.

Sensors

Suitable sensors include, e.g., Schottky (which can be barrier based, but need not be) UV detection diodes, and the like. —calibrated or feedback-only sensors.

Movement Systems

A device can be moved into and within the bore using the patient table; as described elsewhere herein, a device can be engaged with a patient table via a mounting bracket or other connector. A device can also be integrated directly into the patient table; device can also (as described elsewhere herein) be moved into and within the bore using a movement train configured to effect movement of the insertable portion into and within the bore of the medical imaging system. Devices designed with a length sufficient to cover the entire bore can be moved into position and remain static for the duration of the disinfection cycle. Smaller devices can be repositioned to cover the entire bore by translation in iterative steps through the bore using the patient table controlled by dose-feedback and/or MR-console determined speed/pace. A device can also be moved within the bore in a continuous fashion, as opposed to a step-wise fashion. When the device is stationary on the patient bed, the patient bed's movement can be controlled based on the targeted, metered UV-delivery.

Current MRI, CT, and PET imagers have the ability to move the patient tables remotely through proprietary software. One can thus use the patient table to move the UVC device in a similar fashion, either through custom-designed software, manufacturer developed software, or a both. A system can be configured to drive the table (and/or operate the device) based on measurements made by the device, e.g., duration of UVC exposure, intensity of UVC exposure, and the like.

It should be understood that the disclosed systems can be used for one or both of sterilization and disinfection, with sterilization being defined as a process that destroys or eliminate all forms of microbial life (including bacterial spores), and with disinfection being defined as a process that eliminates many or all pathogenic microorganisms except bacterial spores on inanimate objects.

Modeling

Mathematical modeling can be used to determine UVC intensity at the bore and patient table surfaces and to optimize UVC source number and placement for device design to minimize disinfection time. A model can incorporate the digitized cross-section of the bore and patient table surface geometry along with equations to calculate light intensities at these surfaces.

Light intensity at the surface distance from the source can be calculated using the inverse square law for light dispersion, and the Lambert cosine angle can be used to incorporate into the calculations the effect that the angle between the source and surface has on light distribution. Polarization and spectral splitting of light due to the magnetic field strength and their effect on surface intensity are incorporated into the model using experimental data, e.g., data obtained from experiments at various field strengths so as to create an empirical function of source intensity versus magnetic field strength. Individual models can be generated for each size, type, magnetic field strength, and manufacturer of MRI scanners. In addition, the disclosed models can be used for non-MRI equipment such as CT scanners, PET scanners, Spect scanners, or other imaging equipment.

Exemplary model equations are provided below:

$$P_{source} = P_{sensor} \times d_{sensor}^{2}$$

$P_{source}$ = Source power (W/cm$^2$)
$P_{sensor}$ = Sensor measured power (W/cm$^2$)
$d_{sensor}$ = Distance between source and sensor (cm)
Assumes zero-degree angle between source and sensor $$I_{surface}(d) = P_{source}/d_{surface}^{2}$$

$I_{surface}(d)$ = Intensity at surface due to distance (inverse square law of light) (W/cm$^2$)
$d_{surface}$ = Distance between source and surface (cm)

$$I_{surface}(a) = P_{source} \times \cos(\theta)$$

$I_{surface}(a)$ = Intensity at surface due to angle between source and surface (Lambert Cosine Law) (W/cm$^2$)
$\theta$ = Angle between source and surface.

$$I_{surface} = P_{source} \times \cos(\theta)/d_{surface}^{2}$$
Combined a and d $$I_{surface} = P_{source} \times \cos(\theta)/d_{surface}^{2}) \times (FS)$$
(FS) = Function of field strength $$\text{Dose surface} = \int_{0}^{t} I_{surface}(t)\, dt$$

The mathematical model can be used, e.g., in device design to optimize the number and placement of the sources relative to the bore and patient table surfaces. Optimization can be effected by adjusting source placement to maximize the minimal surface intensity calculated from the model. The model can include an iterative method of optimization wherein source placements is determined by maximizing the model equations for surface intensity. Multiple sources and source intensities can be incorporated into the model, and optimization can be based on additional parameters such as power, current, source intensity, etc. The disclosed model can be used for non-MRI equipment such as CT scanners, PET scanners, Spect scanners, or other imaging equipment.

The UVC intensity model can be incorporated into the device to measure the surface intensity and to control the device/patient table motion based on delivered dose. UVC source intensity can be inputted to the model using one or more UVC sensors on the device, which sensors can be optimally positioned on the device. Such sensors can be configured to measure the UVC intensity (e.g., continuously and/or on an interval basis), and the model can in turn calculate the related source intensity based on the known or estimated distance and angle between the sensor and source. From these data, the model can calculate surface intensity and integrates over time to obtain surface dose. When the prescribed (surface) dose is reached, the device controller effects movement of the in-bore UVC device; if the in-bore device is integrated into the medical imaging system, the imaging system moves the patient table to the next position for the in-bore device; the system can also move the in-bore device in a continuous manner until entire bore and table reaches the prescribed dose.

As described, the disclosed models can be used to determine the number and/or locations of UVC radiation sources within an in-bore device. The models can be used to determine the number and/or locations of such sources for in-bore devices that are placed into bores of difference cross-sections, e.g., circular cross-sections vs. oval cross-sections. The disclosed models can also be used to control the operation of a device; as will be apparent, the operation of an in-bore device in a circular bore may be different that the way in which a device may be operated in an oval bore.

Aspects

The following Aspects are illustrative only and do not serve to limit the scope of the present disclosure or the appended claims.

Aspect 1. An instrument treatment system, comprising: an insertable portion, the insertable portion (sometimes referred to as an "in-bore" portion) being configured for insertion into the bore of a medical imaging system, the insertable portion comprising at least one source of UVC radiation, the insertable portion optionally being constructed to be essentially non-interactive with and non-affected by a magnetic field of the medical imaging system.

Aspect 2. The system of Aspect 1, further comprising an input unit that provides one or both of control and power to the source of UVC radiation.

An input unit can be a power supply, a controller (or both), and the like. The input unit can communicate with an external source (and/or with the insertable portion) using hardwire, Wi-Fi, Bluetooth, or other hardware and methods known to those of ordinary skill in the art. As but one example, the insertable portion can be connected to the input unit using a retractable cable system positioned outside the bore.

An input unit can be configured as, e.g., an external controller. Such a controller can control, e.g., UVC dose, movement of the UVC source, intensity of the UVC source, on-off times, and the like. Such data can be logged and transmitted for archiving or further processing. The input unit can be powered by line voltage or internal battery (or both). A battery can be, e.g., non-magnetic or shielded from magnetic field. As mentioned elsewhere herein, an input unit can be part of the insertable portion, but this is not a requirement. (An input unit can be constructed so as to be non-interactive with a magnetic field; an input unit can also be shielded.)

Aspect 3. The system of Aspect 2, wherein the input unit is incorporated into the insertable portion.

Aspect 4. The system of Aspect 2, wherein the input unit is located at a distance from the insertable portion.

Aspect 5. The system of any one of Aspects 2-4, wherein the input unit communicates with the insertable portion via a physical connection.

Aspect 6. The system of any one of Aspects 2-4, wherein the input unit communicates with the insertable portion wirelessly.

Aspect 7. The system of Aspect 2, wherein the input unit modulates UVC dose, modulates movement of the insertable portion, receives a signal from a UVC sensor, or any combination thereof.

Aspect 8. The system of any one of Aspects 2-4, wherein the input unit is constructed to as to be essentially non-interactive with and non-affected by a magnetic field of the medical imaging system.

Aspect 9. The system of Aspect 2, further comprising a connection between the input unit and the source of UVC radiation, the connection being constructed so as to be essentially non-interactive with and non-affected by a magnetic field of the medical imaging system Aspect 10. The system of any one of Aspects 1-9, wherein the insertable portion of the system is configured to be transportable on a patient table of the medical imaging system. The insertable portion can be constructed to attach to patient table using mechanical methods, e.g., straps, Velcro™, and the like. The insertable portion can be, e.g., configured to attach to patient table using a base that matches head coil holder per manufacturer.

Aspect 11. The system of any one of Aspects 1-10, wherein the system comprises a plurality of sources of UVC radiation.

Aspect 12. The system of any one of Aspects 1-11, wherein the insertable portion comprises an enclosure that encloses the at least one source of UVC radiation, the enclosure being essentially transparent to UVC radiation.

Aspect 13. The system of any one of Aspects 1-12, wherein the insertable portion comprises at least one reflector configured to reflect UVC radiation from the at least one source of UVC radiation. The reflector can be configured to optimize reflection to internal bore surfaces and/or optimize UVC dose to a patient table of the imaging system.

Aspect 14. The system of Aspect 13, wherein the insertable portion defines an axis, and wherein the at least one reflector is configured to reflect UVC radiation from the at least one source of UVC radiation in a direction that is essentially radially outward from the axis.

Aspect 15. The system of Aspect 14, wherein the reflector is circular in cross-section.

Aspect 16. The system of any one of Aspects 1-15, further comprising at least one UVC radiation sensor. A system can be controllable based, at least in part, on data collected by the at least one UVC radiation sensor. Other sensor types (e.g., gyroscopes, location sensors, IR sensors, UV sensors besides UVC sensors, visible light sensors, beta radiation sensors, x-ray sensors, gamma radiation sensors, and the like) can all be incorporated into a system according to the present disclosure. A system according to the present disclosure can be controllable and/or operable based at least in part on information gathered by one or more sensors of the system. As an example, if a UVC sensor of a system determines that an insufficient amount of UVC radiation has been emitted, the system can adjust the duration (and/or intensity) of the UVC radiation being delivered. A system can also include a moveable source of UVC radiation (e.g., a source that is rotatable about the circumference of the insertable portion of the system or that is otherwise moveable). The moveable source of UVC radiation can be moved during standard system operation. The moveable source of UVC radiation can also be moveable in response to data collected by a sensor of the system. As but one example, a system can be configured such that if a sensor of the system detects an inadequate level of UVC, a moveable source of UVC radiation can be moved so as to deliver additional UVC radiation to the desired location. The additional UVC radiation can then be monitored by the sensor of the system, with further adjustments to location, duration, and/or intensity of UVC radiation being made as needed.

Aspect 17. The system of any one of Aspects 1-16, wherein the system is configured to be manually transportable.

Aspect 18. The system of any one of Aspects 1-17, further comprising a movement train configured to effect movement of the insertable portion within the bore of the medical imaging system.

Aspect 19. The system of any one of Aspects 1-18, further comprising a processor configured to operate the system so as to effect delivery of a predetermined UVC dose.

Aspect 20. The system of any one of Aspects 1-19, further comprising a processor configured to effect movement of the insertable portion within the bore of the medical imaging system.

Aspect 21. The system of Aspect 22, wherein the movement effects incremental disinfection of two or more discrete regions within the bore.

Aspect 22. The system of any one of Aspects 1-23, wherein the medical imaging system is characterized as a magnetic resonance imaging system, a PET system, a CT system, or an X-ray system.

Aspect 23. The system of any one of Aspects 1-22, further comprising at least one cleaning strip engageable with the insertable portion.

A cleaning strip can comprise an absorbent material, such a sponge or other pervious material. A cleaning strip can also be impregnated with a cleaning solution, such as a disinfectant or other antimicrobial agent. A cleaning strip can be configured such that it contacts the bore of the medical imaging system into which the insertable portion is inserted. A cleaning strip can be reversibly engageable with the insertable portion; an insertable portion can include cleaning strips of different configurations. As an example, an insertable portion can include a first cleaning strip that is wetted with a cleaning solution and also include a second cleaning strip that is dry so as to soak up excess or left-behind cleaning solution from the first cleaning strip. Cleaning strips can be expandable, contractable (e.g., in the manner of a belt) or otherwise changeable in shape and/or size so as to allow for use in bores of varied dimensions.

Aspect 24. The system of any one of Aspects 1-23, further comprising a memory configured to retain one or both of data collected by the system and settings used to control system operation. As described elsewhere herein, data collected by a device according to the present disclosure (and/or the settings used to control such a device) can be archived on the device, on a scanner, in the cloud, or on another storage medium or device. In this way, data and/or settings can be stored and even recalled for future use. Data and settings can also be used to validate device operation, as a user can, for example, determine whether the same given set of settings will, over time, give rise to the same device performance. This can allow a user to monitor the health of a given device; if the same settings used over time do not always result in the same performance (as measured by collected data), a user can monitor device function and determine when device maintenance may be warranted.

Aspect 25. The system of any one of Aspects 1-24, wherein the system is operable in response to a pre-set program of operating conditions.

Aspect 26. The system of any one of Aspects 1-25, wherein the system is operable in response to data collected by the system. Without being bound to any particular theory or embodiment, a system can be operable in response to the output of a model that utilizes data collected by the system. As but one example, a system can be operable based a model's output that is based on estimated UVC dose data generated by the system. As an example, if a system estimates that a prescribed dose of radiation has not been achieved at a certain location or locations of the bore, the in-bore device can be maintained in position and/or the intensity of the UVC radiation emitted by the UVC source can be increased. An instrument treatment system can be configured to generate a dose map of the interior surface of the bore of the medical imaging system; in this way, the instrument treatment system can determine which, if any, locations on the interior surface have not received the prescribed dose of radiation.

Aspect 27. The system of Aspect 26, wherein the data comprise intensity of UVC radiation.

Aspect 28. The system of any one of Aspects 26-27, wherein the system is configured to estimate a UVC dose received by one or more portions of the bore of the medical imaging system.

Aspect 29. The system of any one of Aspects 26-28, wherein the system is configured to modulate a position of the insertable portion within the bore of the medical imaging system, an intensity of UVC radiation delivered by the at least one source of UVC radiation, a duration of UVC radiation delivered by the at least one source of UVC radiation, or any combination thereof.

Aspect 30. A method, comprising operating a system according to any one of Aspects 1-29 so as to eliminate an infective microorganism and/or spore from the bore (and/or table, if present) of the medical imaging system.

Aspect 31. The method of Aspect 30, wherein the operating effects a UVC dose within the bore sufficient to eliminate one or more of influenza, MRSA, a coronavirus, or *Clostridium tetani.*

Aspect 32. The method of Aspect 30, wherein operating effects a UVC dose within the bore sufficient to eliminate all infective microorganisms and spores from the bore.

Aspect 33. A method, comprising: effecting insertion of at least one source of UVC radiation into the bore of a medical imaging system; the at least one source of UVC radiation being essentially non-interactive with a magnetic field of the medical imaging system, operating the at least one source of UVC radiation so as to eliminate an infective microorganism and/or spore from at least a portion of the bore and/or table, if present, of the medical imaging system.

Aspect 34. The method of Aspect 33, wherein the insertion is effected manually.

Aspect 35. The method of Aspect 33, wherein the insertion is effected in an automated fashion.

Aspect 36. The method of any one of Aspects 33-35, wherein the operating is performed so as to effect a predetermined UVC dose. As an example, the operating can be performed to as to effect a UVC dose known to eliminate a particular infective virus.

Aspect 37. The method of any one of Aspects 33-36, wherein the operating is performed to as to effect a UVC dose within the bore sufficient to eliminate one or more of influenza, MRSA, a coronavirus, or *Clostridium tetani.*

Aspect 38. The method of any one of Aspects 33-36, wherein the operating is performed so as to effect a UVC dose within the bore sufficient to eliminate all infective microorganisms and/or spores from the bore.

Aspect 39. The method of any one of Aspects 33-38, wherein the operating is performed, at least in part, based on UVC radiation information collected by at least one UVC radiation sensor. As described elsewhere herein, operating can include, e.g., modulating the duration, intensity, and/or location of UVC radiation delivery. The operating can be in accordance with modeling results, e.g., results from application of a model disclosed herein.

Aspect 40. The method of any one of Aspects 33-39, wherein the insertion effects elimination of an infective microorganism and/or spore from two or more discrete regions within the bore.

Aspect 41. The method of any one of Aspects 33-40, wherein the insertion is effected by a patient table of the medical imaging system.

Aspect 42. The method of any one of Aspects 33-41, wherein the insertion is effected by a movement train in mechanical communication with the source of UVC radiation.

Aspect 43. The method of any one of Aspects 33-42, wherein a processor modulates at least one of the inserting and the operating.

Aspect 44. The method of any one of Aspects 33-43, wherein the source of UVC radiation is modulated by a controller disposed within the bore of the medical imaging system. As explained elsewhere herein, a controller can be disposed outside of the bore of the medical imaging system. UVC radiation can be modulated based on, e.g., one or more signals collected by a sensor within the bore.

Control of the source of UVC radiation can be effected via an interface with the medical imaging system, e.g., in embodiments where the at least one source of UVC radiation is integrated with the medical imaging system. Control of the source of UVC radiation can also be effected through an interface that is independent of the medical imaging system, e.g., via an interface that is dedicated to the source of UVC radiation and is not integrated into the medical imaging system.

Aspect 45. The method of any one of Aspects 33-44, wherein movement of the UVC source effects cleaning of an interior surface of the bore of the medical imaging system. Such cleaning can be accomplished with, e.g., cleaning strips, which are described elsewhere herein.

Aspect 46. The method of any one of Aspects 33-45, further comprising storing one or both of data collected during performance of the method and settings used to control operation of the at least one source of UVC radiation.

Aspect 47. The method of any one of Aspects 33-46, wherein the method is performed according to a pre-set program of operating conditions.

Aspect 48. The method of any one of Aspects 33-47, wherein the method is performed in response to data collected during performance of the method.

Aspect 49. The method of Aspect 48, wherein the data comprise intensity of UVC radiation.

Aspect 50. The method of any one of Aspects 33-49, further comprising estimating a UVC dose received by one or more portions of the bore of the medical imaging system, the estimating optionally being performed in an automated fashion.

Aspect 51. The method of any one of Aspects 33-50, further comprising modulating a position of the insertable portion within the bore of the medical imaging system, an intensity of UVC radiation delivered by the at least one source of UVC radiation, a duration of UVC radiation delivered by the at least one source of UVC radiation, or any combination thereof.

What is claimed:

1. An instrument treatment system, comprising:
an insertable portion,
the insertable portion being configured for insertion into a bore of a medical imaging system,
the insertable portion comprising at least one source of UVC radiation,
the insertable portion being constructed to be essentially non-interactive with and non-affected by a magnetic field of the medical imaging system.

2. The system of claim 1, further comprising an input unit that provides one or both of control or power to the source of UVC radiation.

3. The system of claim 2, wherein the input unit is incorporated into the insertable portion.

4. The system of claim 2, wherein the input unit is located at a distance from the insertable portion.

5. The system of claim 2, wherein the input unit modulates UVC dose, modulates movement of the insertable portion, receives a signal from a UVC sensor, or any combination thereof.

6. The system of claim 2, wherein the input unit is constructed to as to be essentially non-interactive with and non-affected by a magnetic field of the medical imaging system.

7. The system of claim 2, further comprising a connection between the input unit and the source of UVC radiation, the connection being constructed so as to be essentially non-interactive with and non-affected by a magnetic field of the medical imaging system.

8. The system of claim 1, wherein the insertable portion of the system is configured to be transportable on a patient table of the medical imaging system.

9. The system of claim 1, wherein the system comprises a plurality of sources of UVC radiation.

10. The system of claim 1, wherein the insertable portion comprises an enclosure that encloses the at least one source of UVC radiation, the enclosure being essentially transparent to UVC radiation.

11. The system of claim 1, wherein the insertable portion comprises at least one reflector configured to reflect UVC radiation from the at least one source of UVC radiation.

12. The system of claim 11, wherein the insertable portion defines an axis, and wherein the at least one reflector is configured to reflect UVC radiation from the at least one source of UVC radiation in a direction that is essentially radially outward from the axis.

13. The system of claim 1, further comprising at least one UVC radiation sensor.

14. The system of claim 1, further comprising a movement train configured to effect movement of the insertable portion within the bore of the medical imaging system.

15. The system of claim 1, wherein the medical imaging system is characterized as a magnetic resonance imaging system, a PET system, a CT system, or an X-ray system.

16. The system of claim 1, further comprising at least one cleaning strip engageable with the insertable portion.

17. The system of claim 1, further comprising a memory configured to retain one or both of data collected by the system and settings used to control system operation.

18. The system of claim 1, wherein the system is operable in response to a pre-set program of operating conditions.

19. The system of claim 1, wherein the system is operable in response to data collected by the system.

20. The system of claim 19, wherein the data comprise intensity of UVC radiation.

21. The system of claim 19, wherein the system is configured to estimate a UVC dose received by one or more portions of the bore of the medical imaging system.

22. The system of claim 19, wherein the system is configured to modulate a position of the insertable portion within the bore of the medical imaging system, an intensity of UVC radiation delivered by the at least one source of UVC radiation, a duration of UVC radiation delivered by the at least one source of UVC radiation, or any combination thereof.

23. A method, comprising:
inserting an instrument treatment system into a bore of a medical imaging system and operating the instrument treatment system so as to eliminate an infective microorganism and/or a spore from the bore, table if present, or both of the medical imaging system,
the instrument treatment system comprising:
an insertable portion,
the insertable portion being configured for insertion into the bore of the medical imaging system,
the insertable portion comprising at least one source of UVC radiation, and
the insertable portion being constructed to be essentially non-interactive with and non-affected by a magnetic field of the medical imaging system.

24. A method, comprising:
effecting insertion of at least one source of UVC radiation into the bore of a medical imaging system;
the at least one source of UVC radiation being essentially non-interactive with a magnetic field of the medical imaging system,
operating the at least one source of UVC radiation so as to eliminate an infective microorganism and/or spore from at least a portion of the bore and/or table, if present, of the medical imaging system.

25. The method of claim 24, wherein the operating is performed, at least in part, based on UVC radiation information collected by at least one UVC radiation sensor.

26. The method of claim 24, wherein the insertion is effected by a patient table of the medical imaging system.

27. The method of claim 24, wherein the insertion is effected by a movement train in mechanical communication with the source of UVC radiation.

28. The method of claim 24, wherein the method is performed in response to data collected during performance of the method.

29. The method of claim 24, further comprising estimating a UVC dose received by one or more portions of the bore of the medical imaging system.

30. The method of claim 24, further comprising modulating a position of the insertable portion within the bore of the medical imaging system, an intensity of UVC radiation delivered by the at least one source of UVC radiation, a duration of UVC radiation delivered by the at least one source of UVC radiation, or any combination thereof.

* * * * *